(12) United States Patent
Fojtik

(10) Patent No.: US 12,171,456 B2
(45) Date of Patent: Dec. 24, 2024

(54) APPARATUS FOR ROTATING MEDICAL DEVICES, SYSTEMS INCLUDING THE APPARATUS, AND ASSOCIATED METHODS

(71) Applicant: MINERVA SURGICAL, INC., Santa Clara, CA (US)

(72) Inventor: Shawn P. Fojtik, Park City, UT (US)

(73) Assignee: MINERVA SURGICAL, INC., Santa Clara, CA (US)

( * ) Notice: Subject to any disclaimer, the term of this patent is extended or adjusted under 35 U.S.C. 154(b) by 796 days.

(21) Appl. No.: 17/235,438

(22) Filed: Apr. 20, 2021

(65) Prior Publication Data

US 2021/0236159 A1 Aug. 5, 2021

Related U.S. Application Data

(63) Continuation of application No. 14/076,170, filed on Nov. 8, 2013, now Pat. No. 11,000,307, which is a (Continued)

(51) Int. Cl.
*A61B 17/00* (2006.01)
*A61B 17/16* (2006.01)
(Continued)

(52) U.S. Cl.
CPC .. *A61B 17/320758* (2013.01); *A61B 17/1626* (2013.01); *A61M 25/01* (2013.01);
(Continued)

(58) Field of Classification Search
CPC .......... A61B 17/00; A16B 2017/00367; A16B 2017/00407
See application file for complete search history.

(56) References Cited

U.S. PATENT DOCUMENTS 24,005 A 5/1859 Brooks
54,069 A 4/1866 Hartford
(Continued)

FOREIGN PATENT DOCUMENTS

DE 3804849 A1 9/1988
JP 2003290238 A 10/2003
(Continued)

OTHER PUBLICATIONS

US 2001/0041889 A1, 11/2001, Foster (withdrawn)
(Continued)

*Primary Examiner* — John R Downey
(74) *Attorney, Agent, or Firm* — Seager, Tufte & Wickhem, LLP

(57) ABSTRACT

A rooter includes a rotatable element, an actuator for causing the rotatable element to rotate, and a coupling feature for rotatably coupling an elongated medical instrument to the rotatable element. The rotatable element may be at least partially contained within the interior of a housing or another element that remains substantially stationary as the actuator causes the rotatable element to rotate. The rooter may be used with a variety of elongated medical instruments, such as wires, mascerators, needles, drill bits, trocars, catheters, tubes and other elongated instruments that are used to enable or effect medical procedures within the body of a subject. The rooter may be used for a variety of purposes, including, without limitation, the introduction of an elongated medical instrument into the body of a subject or its removal from the subject's body; removing, breaking up, or eliminating obstructions (e.g., blood clots, plaques, etc.) from the body of a subject; and obtaining samples from a subject's body.

19 Claims, 9 Drawing Sheets

Related U.S. Application Data continuation-in-part of application No. 13/039,831, filed on Mar. 3, 2011, now Pat. No. 9,107,691, which is a continuation-in-part of application No. 12/907,926, filed on Oct. 19, 2010, now Pat. No. 8,845,621.

(60) Provisional application No. 61/723,781, filed on Nov. 8, 2012.

(51) Int. Cl.
    *A61B 17/3207*    (2006.01)
    *A61M 25/01*      (2006.01)
    *A61M 25/09*      (2006.01)
    *A61B 17/22*      (2006.01)
    *A61B 17/29*      (2006.01)
    *A61B 17/32*      (2006.01)
    *A61B 17/34*      (2006.01)

(52) U.S. Cl.
CPC ... *A61M 25/09* (2013.01); *A61B 2017/00367* (2013.01); *A61B 2017/0046* (2013.01); *A61B 2017/00469* (2013.01); *A61B 17/1624* (2013.01); *A61B 2017/22094* (2013.01); *A61B 2017/2903* (2013.01); *A61B 17/32002* (2013.01); *A61B 2017/320775* (2013.01); *A61B 2017/3409* (2013.01); *A61M 25/0113* (2013.01); *A61M 2025/09116* (2013.01)

(56) References Cited

U.S. PATENT DOCUMENTS

| | | | |
|---|---|---|---|
| 377,783 | A | 2/1888 | Shaver |
| 383,031 | A | 5/1888 | Allgoever |
| 385,414 | A | 7/1888 | Huber |
| 505,165 | A | 9/1893 | Hughes |
| 515,327 | A | 2/1894 | Eggert |
| 532,145 | A | 1/1895 | Defatsch |
| 537,681 | A | 4/1895 | Furbish |
| 543,096 | A | 7/1895 | Jones |
| 560,281 | A | 5/1896 | Rauhoff |
| 568,460 | A | 9/1896 | Schay |
| 575,734 | A | 1/1897 | Rauhoff |
| 597,766 | A | 1/1898 | Furbish |
| 621,401 | A | 3/1899 | Davis |
| 624,122 | A | 5/1899 | Stevenson |
| 652,137 | A | 6/1900 | Olson |
| 654,150 | A | 7/1900 | Hanna et al. |
| 666,508 | A | 1/1901 | Furbish |
| 674,719 | A | 5/1901 | Woodruff |
| 685,678 | A | 10/1901 | Furbish |
| 700,970 | A | 5/1902 | Mcfarland |
| 711,169 | A | 10/1902 | Leblanc |
| 722,332 | A | 3/1903 | Stump |
| 756,388 | A | 4/1904 | May |
| 791,766 | A | 6/1905 | Furbish |
| 791,767 | A | 6/1905 | Furbish |
| 819,536 | A | 5/1906 | Furbish |
| 873,296 | A | 12/1907 | Chappelle |
| 924,372 | A | 6/1909 | Peck |
| 924,878 | A | 6/1909 | Baron |
| 938,341 | A | 10/1909 | Ruple |
| 942,571 | A | 12/1909 | Leland et al. |
| 942,572 | A | 12/1909 | Leland |
| 973,881 | A | 10/1910 | Rioux |
| 979,939 | A | 12/1910 | Peglev et al. |
| 1,023,023 | A | 4/1912 | Wolin |
| 1,024,960 | A | 4/1912 | Leopold |
| 1,033,615 | A | 7/1912 | Peck |
| 1,054,142 | A | 2/1913 | Plein |
| 1,061,773 | A | 5/1913 | Nahlinger |
| 1,104,210 | A | 7/1914 | Meredith |
| 1,104,863 | A | 7/1914 | Baldwin |
| 1,134,511 | A | 4/1915 | Carlson |
| 1,183,426 | A | 5/1916 | Booth |
| 1,188,162 | A | 6/1916 | Duggan |
| 1,206,589 | A | 11/1916 | Pipshik |
| 1,268,309 | A | 6/1918 | White |
| 1,290,489 | A | 1/1919 | Bauer |
| 1,304,714 | A | 5/1919 | Starrett |
| 1,330,053 | A | 2/1920 | Booth |
| 1,415,251 | A | 5/1922 | Mclean |
| 1,415,822 | A | 5/1922 | Fegley et al. |
| 1,422,411 | A | 7/1922 | Borick |
| 1,460,201 | A | 6/1923 | Leopold |
| 1,477,337 | A | 12/1923 | Fegley |
| 1,497,479 | A | 6/1924 | Booth |
| 1,516,443 | A | 11/1924 | Leopold |
| 1,531,086 | A | 3/1925 | Fegley et al. |
| 1,578,866 | A | 3/1926 | Swain |
| 1,704,067 | A | 3/1929 | Wick |
| 1,821,194 | A | 9/1931 | Wilcox |
| 1,838,957 | A | 12/1931 | Orawiec |
| 1,904,679 | A | 4/1933 | Fegley et al. |
| 1,971,289 | A | 8/1934 | Abramson et al. |
| 1,971,290 | A | 8/1934 | Abramson et al. |
| 3,049,018 | A | 8/1962 | Lusskin et al. |
| 3,619,081 | A | 11/1971 | Gruska et al. |
| 3,869,936 | A | 3/1975 | Taillardat |
| 3,955,578 | A | 5/1976 | Chamness et al. |
| 4,273,128 | A | 6/1981 | Lary |
| 4,306,599 | A | 12/1981 | Kurahashi |
| 4,343,200 | A | 8/1982 | Alworth et al. |
| 4,524,650 | A | 6/1985 | Marks |
| 4,611,594 | A | 9/1986 | Grayhack et al. |
| 4,685,344 | A | 8/1987 | Horn et al. |
| 4,694,838 | A | 9/1987 | Wijayarthna et al. |
| 4,850,957 | A | 7/1989 | Summers |
| 4,926,858 | A | 5/1990 | Gifford, III et al. |
| 5,024,565 | A | 6/1991 | Pinand |
| 5,079,963 | A | 1/1992 | Yamamoto et al. |
| 5,087,265 | A | 2/1992 | Summers |
| 5,195,954 | A | 3/1993 | Scnepp-Pesch et al. |
| 5,217,474 | A | 6/1993 | Zacca et al. |
| 5,251,120 | A | 10/1993 | Smith |
| 5,376,100 | A | 12/1994 | Lefebvre |
| 5,498,258 | A | 3/1996 | Hakky et al. |
| 5,527,326 | A | 6/1996 | Hermann et al. |
| 5,591,187 | A | 1/1997 | Dekel |
| 5,674,235 | A | 10/1997 | Parisi |
| 5,787,953 | A | 8/1998 | Jacobson |
| 5,843,103 | A | 12/1998 | Wulfman |
| 5,855,586 | A | 1/1999 | Habara et al. |
| 5,911,722 | A | 6/1999 | Adler et al. |
| 5,988,006 | A | 11/1999 | Fleytman |
| 6,001,112 | A | 12/1999 | Taylor |
| 6,015,381 | A | 1/2000 | Ouchi |
| 6,090,118 | A | 7/2000 | Mcguckin, Jr. |
| 6,156,046 | A | 12/2000 | Passafaro et al. |
| 6,217,595 | B1 | 4/2001 | Shturman et al. |
| 6,258,101 | B1 | 7/2001 | Blake, III |
| 6,270,508 | B1 | 8/2001 | Klieman et al. |
| 6,602,262 | B2 | 8/2003 | Griego et al. |
| 6,602,264 | B1 | 8/2003 | Mcguckin, Jr. |
| 6,685,722 | B1 | 2/2004 | Rosenbluth et al. |
| 6,824,550 | B1 | 11/2004 | Noriega et al. |
| 6,926,725 | B2 | 8/2005 | Cooke et al. |
| 6,997,926 | B2 | 2/2006 | Gellman et al. |
| 7,037,316 | B2 | 5/2006 | Mcguckin, Jr. et al. |
| 7,041,116 | B2 | 5/2006 | Goto et al. |
| 7,101,378 | B2 | 9/2006 | Salameh et al. |
| 7,179,269 | B2 | 2/2007 | Welch et al. |
| 7,276,067 | B2 | 10/2007 | Bales et al. |
| D556,527 | S | 12/2007 | Russo et al. |
| 7,326,203 | B2 | 2/2008 | Papineau et al. |
| 7,357,287 | B2 | 4/2008 | Shelton et al. |
| 7,507,246 | B2 | 3/2009 | Mcguckin et al. |
| 7,559,934 | B2 | 7/2009 | Teague et al. |
| 7,575,585 | B2 | 8/2009 | Goto et al. |
| 7,621,923 | B2 | 11/2009 | Goldenberg |
| 7,722,613 | B2 | 5/2010 | Sutterlin et al. |
| 7,753,919 | B2 | 7/2010 | Kanamaru |
| 7,819,887 | B2 | 10/2010 | Mcguckin, Jr. et al. |

(56) References Cited

U.S. PATENT DOCUMENTS

| | | |
|---|---|---|
| 7,822,458 B2 | 10/2010 | Webster et al. |
| 7,938,851 B2 | 5/2011 | Olson et al. |
| 7,946,198 B2 | 5/2011 | Gui et al. |
| 7,999,680 B2 | 8/2011 | Penot |
| 8,043,303 B2 | 10/2011 | Razvi et al. |
| 8,062,317 B2 | 11/2011 | Mcguckin, Jr. et al. |
| 8,125,097 B1 | 2/2012 | Lomerson, Sr. et al. |
| 8,251,119 B2 | 8/2012 | Toti et al. |
| 8,298,257 B2 | 10/2012 | Sepetka et al. |
| 8,414,543 B2 | 4/2013 | Mcguckin, Jr. et al. |
| 2002/0069715 A1 | 6/2002 | Genco |
| 2002/0117534 A1 | 8/2002 | Green et al. |
| 2004/0064136 A1 | 4/2004 | Papineau et al. |
| 2005/0119615 A1 | 6/2005 | Noriega et al. |
| 2005/0143653 A1 | 6/2005 | Fukuda |
| 2005/0267323 A1 | 12/2005 | Dorros et al. |
| 2005/0273147 A1 | 12/2005 | Israel |
| 2006/0106407 A1 | 5/2006 | McGuckin et al. |
| 2006/0206128 A1 | 9/2006 | Conquergood et al. |
| 2006/0247607 A1 | 11/2006 | Cornelius et al. |
| 2007/0149893 A1 | 6/2007 | Heske et al. |
| 2007/0213634 A1 | 9/2007 | Teague |
| 2007/0265633 A1 | 11/2007 | Moon et al. |
| 2008/0033467 A1 | 2/2008 | Miyamoto et al. |
| 2008/0103504 A1 | 5/2008 | Schmitz et al. |
| 2008/0277445 A1 | 11/2008 | Zergiebel et al. |
| 2009/0270862 A1 | 10/2009 | Arcenio |
| 2009/0275970 A1 | 11/2009 | Leibowitz |
| 2011/0152920 A1 | 6/2011 | Eckhouse et al. |
| 2011/0282370 A1 | 11/2011 | Levine et al. |
| 2012/0095447 A1 | 4/2012 | Fojtik |
| 2012/0191119 A1 | 7/2012 | Hedstrom et al. |
| 2012/0238905 A1 | 9/2012 | Heske et al. |
| 2012/0239008 A1 | 9/2012 | Fojtik |
| 2012/0239064 A1 | 9/2012 | Cartier et al. |
| 2012/0253186 A1 | 10/2012 | Simpson et al. |
| 2013/0317529 A1 | 11/2013 | Golden et al. |
| 2015/0305765 A1 | 10/2015 | Fojtik et al. |

FOREIGN PATENT DOCUMENTS

| | | | |
|---|---|---|---|
| JP | 2007301392 A | 11/2007 | |
| JP | 2007325925 A | 12/2007 | |
| JP | 2008520351 A | 6/2008 | |
| JP | 2008272488 A | 11/2008 | |
| JP | 2010503479 A | 2/2010 | |
| RO | 117079 B1 | 10/2001 | |
| WO | 9611638 A1 | 4/1996 | |
| WO | 9717027 A1 | 5/1997 | |
| WO | 2008033983 A1 | 3/2008 | |
| WO | 2010115134 A1 | 10/2010 | |

OTHER PUBLICATIONS

BCMA Medical Museum, Bone Drill Exhibit (1914-1930), BCMA Website http://bcmamedicalmuseum.org/object/993.1220.1 (Feb. 9. 2009 vesion).

Wentzell, "Machine Design, Power Screws and Ball Screws," Thomson Delmar Learning, (obtained from http://www.uni.edu/~rao/MD-18%20Power%20screws.pdf. on Dec, 6, 2013). 2004.

Nagyszalanczy, "The Art of Fine Tools," The Taunton Press, 2000 BCMA Medical Museum, 993.1220.1: Bone Drill 1914-1930, Feb. 9, 2009 (obtained from http://web.archive.org/web/20090209060158/http://bcmamedicalmuseum.org/object/993.1220.1).

Eggert, Chapter 13: Power Screws, "Engineering Design," McGraw-Hill, 2004.

U.S. Patent and Trademark Office "International Search Report" issued in corresponding PCT/US2011/056892, Jan. 30, 2012.

U.S. Patent and Trademark Office as the International Searching Authority, "International Search Report and Written Opinion," mailed Apr. 4, 2014, in corresponding PCT application PCT/US2013/069350.

The Crystal Reference Encyclopedia, Nitinol, 2005.

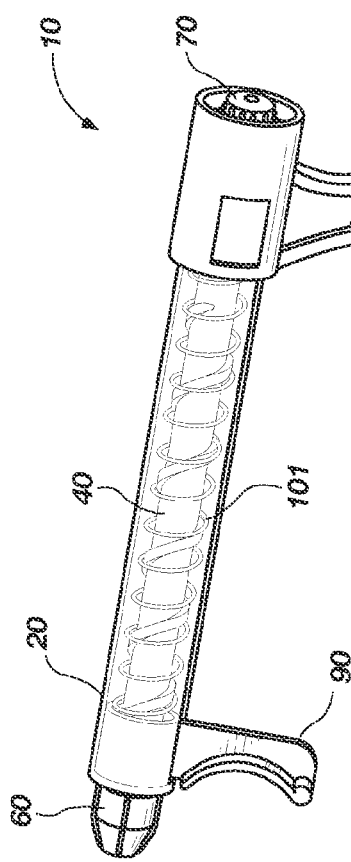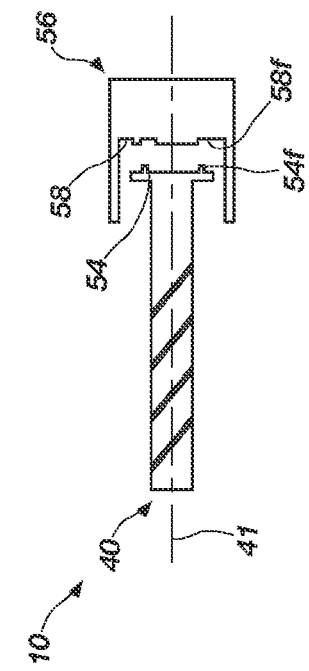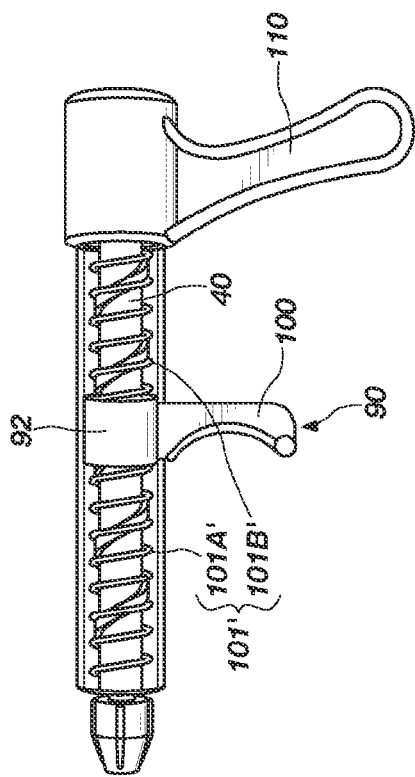
FIG. 1
FIG. 1B
FIG. 1A

APPARATUS FOR ROTATING MEDICAL DEVICES, SYSTEMS INCLUDING THE APPARATUS, AND ASSOCIATED METHODS

CROSS-REFERENCE TO RELATED APPLICATIONS

This application is a continuation of U.S. application Ser. No. 14/076,170 filed Nov. 8, 2013 which claims the benefit of U.S. Provisional Ser. No. 61/723,781, filed Nov. 8, 2012 pursuant to 35 U.S.C. § 119(e). This application is also a continuation-in-part of U.S. patent application Ser. No. 13/039,831, filed on Mar. 3, 2011, now U.S. Pat. No. 9,107,691, and which is a continuation-in-part of U.S. patent application Ser. No. 12/907,926, filed on Oct. 19, 2010, now U.S. Pat. No. 8,465,621. The entire disclosure of each of the foregoing applications is hereby incorporated herein.

TECHNICAL FIELD

This disclosure relates generally to apparatuses and methods for rotating, or spinning, rotatably oscillating and/or inducing back and forth longitudinal movement in medical devices and, more specifically, to apparatuses and methods for manually spinning, oscillating and/or back-and-forth longitudinal movement in elongated medical instruments. In particular, apparatuses and methods for spinning, oscillating and/or inducing back and forth longitudinal movement in wires, mascerators, needles, drill bits, trocars, catheters and other elongated medical devices that may be used to enable or effect a medical procedure within the body of a subject.

SUMMARY

In one aspect, the present disclosure includes various embodiments of an apparatus for causing an elongated medical instrument to rotate, or spin, about its longitudinal axis. Such an apparatus may be referred to herein as a "rooter." In a specific embodiment, such an apparatus includes a housing, a rotatable element within the housing, retention elements for securing the rotatable element in place relative to the housing, and an actuator that causes the rotatable element to rotate within the housing.

The rotatable element may be configured to engage an elongated medical instrument, such as a wire, a mascerator, a needle, a drill bit, a trocar, a catheter or another elongated element that may be used to enable or effect a medical procedure within the body of a subject. In various embodiments, at least one end of the rotatable element, which is accessible from an end of the housing, may be configured to receive and retain the elongated medical instrument. In some embodiments, the rotatable element may comprise an elongated member with a longitudinal axis, about which the rotatable element may rotate, or spin. In a more specific embodiment, the rotatable element may include a helical ridge, similar to the thread of a bolt or screw.

The rotatable element may be disposed within an interior of the housing in a manner that enables the rotatable element to spin about its longitudinal axis. As the rotatable element rotates within the housing, which may remain substantially stationary (e.g., within a user's grasp, etc.) a medical element engaged by the rotatable element may rotate.

An actuator may be associated with the rotatable element in such a way as to cause the rotatable element to rotate. In a specific embodiment, the actuator may include an external element configured for manual operation, as well as an internal element that interacts with the rotatable element.

The actuator may be disposed around at least a portion of the rotatable element. In embodiments where the rotatable element has a helical ridge, the internal element of the actuator may be positioned between longitudinally adjacent locations of the helical ridge. In other embodiments, an actuator may include one or more grooves that are configured complementarily to and cooperate with the helical ridge. The actuator may move longitudinally relative to the rotatable element (e.g., in directions substantially parallel to the rotational axis of the rotatable element, etc.), while the internal element of the actuator and the helical ridge of the rotatable element interact with one another to cause the rotatable element, as well as any medical element engaged thereby, to rotate, or spin.

Longitudinal movement of the actuator may be enabled by one or more elongated slots that extend through the housing, along at least a portion of its length. Movement of the external element and the intermediate element drives movement of the actuator along a length of the rotatable element. In embodiments where the external element and/or the intermediate element pivot relative to the actuator, the axis about which such pivoting occurs may be oriented perpendicular to and extend through an axis about which the rotatable element rotates. This configuration may impart the rooter with stability and prevent binding as the actuator moves back and forth along the length of the rotatable element. The elongated slot may receive an intermediate element of the actuator, holding the actuator in place as it is moved along the length of the rotatable element.

Various embodiments of macerator wires are also within the scope of this disclosure. A macerator wire may include one or more non-linear features at or near its distal end. Each non-linear feature may be located beyond an axis of a remainder of the macerator wire. In some embodiments, the non-linear feature may define a distal-most end of the macerator wire. In some such embodiments, the distal-most end defined by the non-linear feature may be smooth (e.g., rounded, etc.) to facilitate its introduction into and movement through the body of a subject.

This disclosure also includes systems for effecting medical processes. A system of this disclosure includes a rooter, as well as an elongated medical instrument, such as a wire, a macerator, a needle, a drill bit, a trocar, a catheter or another elongated element that may be used to enable or effect a medical procedure within the body of a subject, associated with the rooter. The rooter may be manually operable. As the rooter operates, it causes the elongated medical instrument to rotate or spin.

A system for rotating one or more elongated medical instruments may include a rooter, a branched coupling element (e.g., a Y-connector, a T-connector, etc.), one or more elongated medical instruments and another medical device. In a specific embodiment, a first elongated medical instrument, such as a wire, a macerator or a small catheter, may be rotationally coupled to the rotational element of the rooter. A proximal end of the branched coupling element may be positioned adjacent to the distal end of the rotational element, but remain rotationally uncoupled from the rotational element. A proximal end of a second elongated medical instrument, such as a catheter or other conduit, which resides coaxially over the first elongated medical instrument, may be coupled to a distal end of the branched coupling element. Another medical device, such as a syringe, an aspirator, or the like, may be coupled to the branch of the branched connector and, thus, communicate with the second elongated medical instrument through the branched connector. In such an arrangement, the rooter may be used to cause the first elongated medical instrument to rotate, while the other medical device introduces material into and/or withdraws material from the second elongated medical instrument.

In another aspect, methods for rotating, or spinning, elongated medical instruments are disclosed, as are methods for inducing oscillatory (i.e., alternating between clockwise and counterclockwise rotation) or vibration-like movement, longitudinal movement (e.g., a back-and-forth hammering action, etc.) and other movements in elongated medical instruments are disclosed. In such a method, an elongated medical instrument is associated with (e.g., engaged by, etc.) a rotatable element of a rooter. Manual operation of an actuator of the rooter (e.g., with a user's thumb or finger, etc.) causes the rotatable element, along with the elongated medical instrument that has been secured to the rotatable element, to rotate or spin. The rotatable element may be rotated continuously in a single direction (e.g., clockwise or counterclockwise), or it may be rotated in an alternating or oscillating fashion (i.e., one direction, then another).

Without limitation, oscillatory rotation of a wire (e.g., a guide wire, a mascerator, etc.) may be used to introduce the wire through a blockage, narrowing, tortuosity or other feature or obstruction. By oscillating a wire, its alternating rotation may enable it to "find" and/or follow the path of least resistance through a blockage, narrowing, tortuosity or other feature. In many cases, the path of least resistance will be tortuous. For example, a vessel, tube, catheter or the like may define or follow a somewhat tortuous path. The path of least resistance of a blockage of a relatively straight portion of a vessel, tube or catheter may also be somewhat tortuous, as blockages are often nonhomogeneous, including combinations of hard and soft regions.

In some embodiments, movement of the rotatable element of a rooter and any elongated medical instrument coupled thereto may be accompanied by longitudinal movement of the rotatable element and any elongated medical instrument in one or more directions. When the rotatable element is oscillated, this longitudinal movement may include a repeated back-and-forth movement, inducing a hammering action in the rotatable element and any elongated medical instrument that has been coupled thereto. This hammering action may be used alone or in conjunction with oscillation of an elongated medical instrument to facilitate its introduction into or through a structure (e.g., a blockage, such as arterial plaque; a calcification; bone; etc.).

Rotation, oscillation, hammering or other movement of the elongated medical instrument may be used to effect a variety of medical procedures, depending at least in part upon the type of elongated medical instrument that has been assembled with the rooter. Some specific, but non-liming embodiments of procedures in which a rooter may be used include, but are not limited to, "first-use" techniques, in which a guide wire is oscillated. Oscillatory movement of a guide wire may enable the guide wire to penetrate a blockage (e.g., a plaque, a calcified or resistant lesion, etc.) in a controlled manner. Oscillation of a guide wire may also enable a distal tip of the guide wire to quickly probe a plurality of locations, which facilitates "finding" or identifying paths of least resistance through blockages and tortuous paths. Oscillation may also reduce the tendency of a guide wire or other elongated medical instrument from binding the internal surfaces of a path, such as a vessel, a path through a blockage, a catheter or a tube. Oscillation of a guide wire during its movement through a vessel, catheter or tube may also reduce the risk of perforating a vessel, catheter or tube.

A system that includes a rooter and a guide wire or mascerator may be used in catheterization procedures, in thrombus (including deep vein thrombosis—DVT) management (i.e., masceration and removal), to clear catheters and tubes (e.g., feeding tubes, drainage tubes, PTFE (polytetrafluoroethylene) grafts for hemodialysis access, etc.) and for a variety of other purposes.

Other aspects, as well as features and advantages of various aspects, of the disclosed subject matter will become apparent to those of skill in the art from consideration of the ensuing description, the accompanying drawings, and the appended claims.

BRIEF DESCRIPTION OF THE DRAWINGS

In the drawings:

FIG. 1 is a perspective view of an embodiment of rooter of this disclosure;

FIGS. 1A and 1B show variations of the embodiment of rooter depicted by FIG. 1;

DETAILED DESCRIPTION

Figure 2:
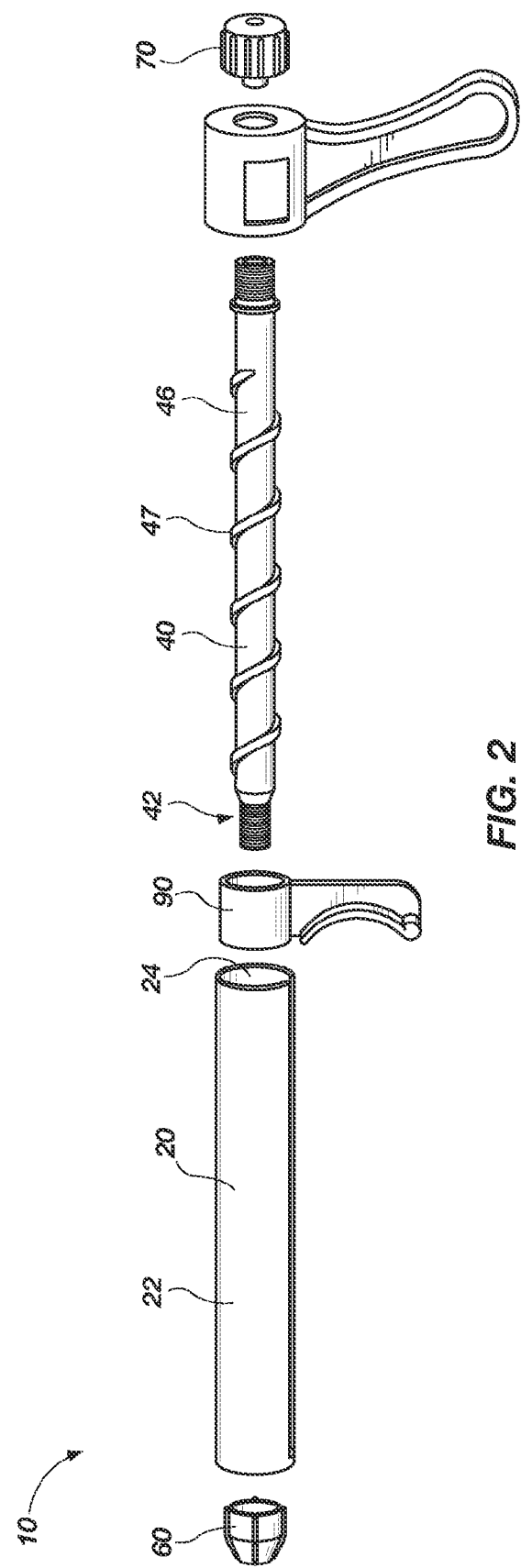
FIG. 2 is an exploded view of the embodiment of rooter shown by FIG. 1.

With reference to FIGS. 1 and 2, an embodiment of rooter 10 that incorporates teachings of this disclosure is illustrated. Rooter 10 includes a housing 20, a rotatable element 40, a distal retention element 60 and a proximal retention element 70, and an actuator 90.

Figures 3A, 3B, 3C:
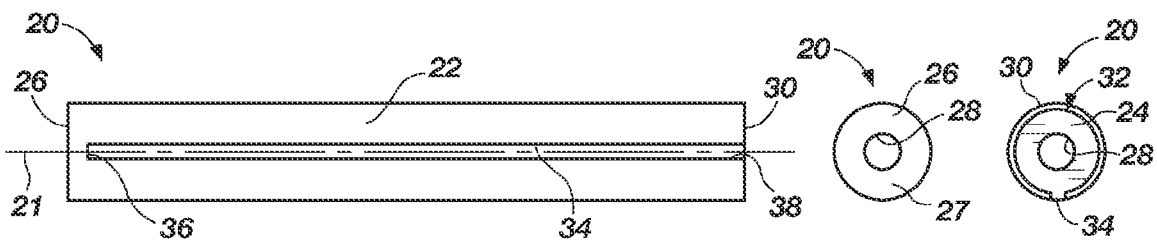
FIGS. 3A, 3B, and 3C are, respectively, bottom, distal end, and proximal end views of a housing of the embodiment of rooter depicted by FIGS. 1 and 2.

The housing 20, which is also shown in FIGS. 3A-3C, is an elongated element with an exterior 22 and a hollow interior 24. In the depicted embodiment, the housing 20 is cylindrical in shape, with a longitudinal axis 21 extending centrally through the length of the housing 20. The housing 20 includes a distal end 26 and an opposite, proximal end 30. A longitudinal slot 34 extends along a portion of the length of the housing 20.

The distal end 26, which is the end of the housing 20 that may be located farthest from an individual during use of the rooter 10 (FIGS. 1 and 2), is partially closed, as depicted by FIG. 3B. In a specific embodiment, the distal end 26 may include a circumferential lip 27 that defines an opening 28, which extends through the housing 20, from its exterior 22 to its interior 24. The opening 28 may be centered about the longitudinal axis 21 of the housing 20.

As seen in FIG. 3C, the proximal end 30 of the housing 20, which may be located closest to the individual during operation of the rooter 10, may include an opening 32 that exposes the interior 24 of the housing 20. In some embodiments, the proximal end 30 of the housing 20 may be configured to receive a cap 56 (FIGS. 5A-5C), which may at least partially close the opening 32 at the proximal end 30.

The longitudinal slot 34, illustrated in FIGS. 3A and 3C, extends through a wall of the housing 20, from the exterior 22 of the housing 20 to the interior 24 of the housing 20. In the embodiment depicted by FIG. 3A, the longitudinal slot 34 is substantially linear. A distal end 36 of the longitudinal slot 34 may be located adjacent to, but proximally spaced apart from, the distal end 26 of the housing 20. An opposite, proximal end 38 of the longitudinal slot 34 is located at or near (i.e., distally spaced apart from) the proximal end 30 of the housing 20.

Figures 4A, 4B, 4C:
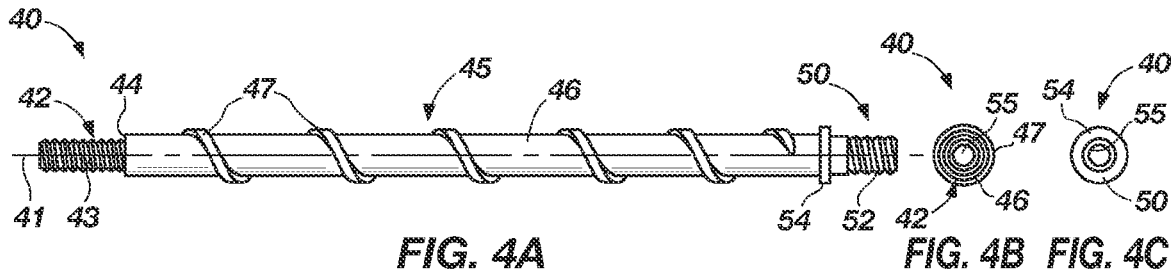
FIGS. 4A, 4B, and 4C are, respectively, side, distal end, and proximal end views of a rotatable element of the embodiment of rooter shown in FIGS. 1 and 2.

The rotatable element 40 of the embodiment of rooter 10 (FIGS. 1 and 2) illustrated by FIGS. 4A-4C is an elongated element that is configured to be assembled with the housing 20 (FIGS. 3A-3C) of the rooter 10. In some embodiments, the rotatable element 40 may be tubular and, thus, include a conduit 55 extending through a portion of its length or through its entire length. A longitudinal axis 41 of the rotatable element 40 extends centrally or substantially centrally through a length of the rotatable element 40. In embodiments where the rotatable element 40 includes a conduit 55, the conduit 55 and the longitudinal axis 41 of the rotatable element 40 may be aligned (e.g., concentric, etc.).

In embodiments where the rotatable element 40 includes a conduit 55, the conduit 55 may enable flow communication between the interior of a hollow elongated medical instrument (e.g., a needle, catheter, etc.) to be coupled to the rooter 10 and a separate flow facilitating apparatus (e.g., a syringe, an aspiration device, and infusion device, a vacuum line, etc.).

In some embodiments, the conduit 55 through the rotatable element 40 may be configured to receive the elongated medical instrument. The conduit 55 may be configured in such a way that a portion of an elongated medical instrument 200 (see FIG. 17) may extend partially or completely through a length of the rotatable element 40. Some non-limiting examples of elongated medical instruments that may be received by the rotatable element 40 include, but are not limited to, wires, mascerators, needles, drill bits, trocars, catheters, tubes or the like.

Figure 17:
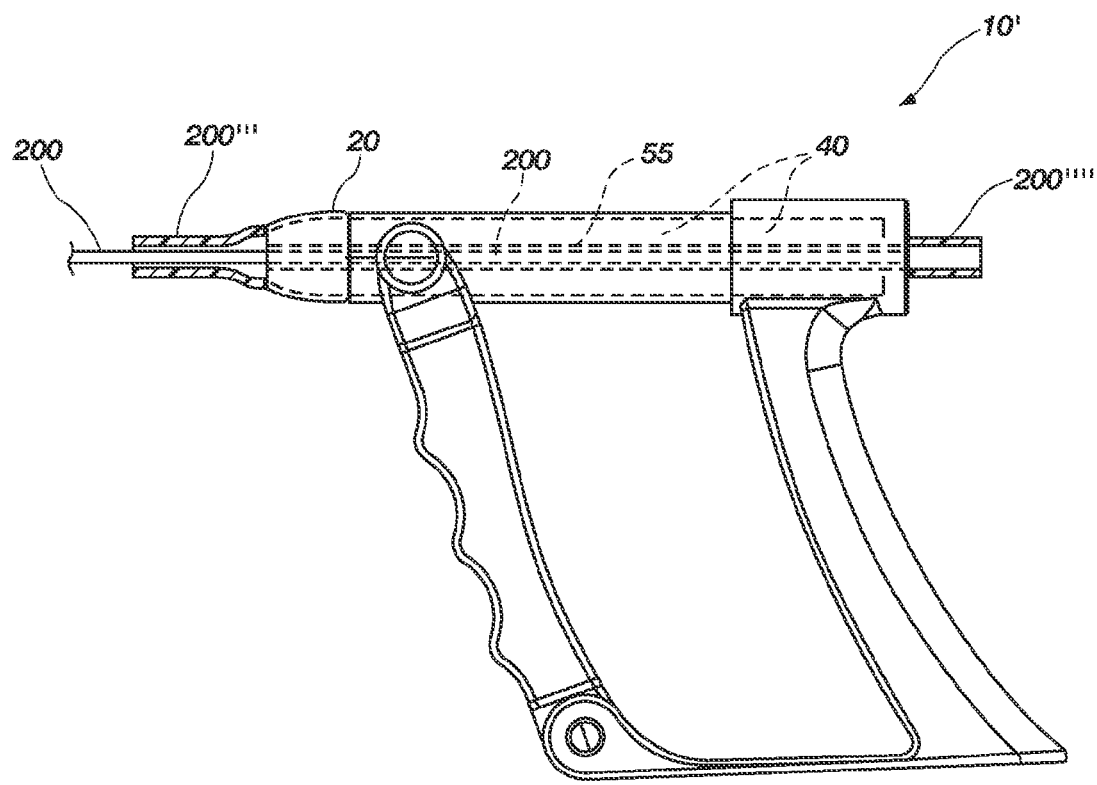
FIG. 17 illustrates the manners in which one or more elongated medical instruments may be assembled or otherwise associated with a rooter according to this disclosure.

In some embodiments, as illustrated by FIG. 17, the elongated medical instrument 200 that extends through at least a portion of the rotatable element 40 may also extend into, or even through, another elongated medical instrument 200''' that has been secured to a distal end (i.e., the end closest to a subject) of the rooter 10'. Depending upon whether or not the elongated medical instrument 200 and the other elongated medical instrument 200''' are coupled with or engaged by the rotatable element 40, one or both of them may rotate when the rotatable element 40 rotates. An elongated medical instrument 200, 200''' that is coupled to or engaged by the rotatable element 40 will rotate when the rotatable element 40 rotates, while an elongated medical instrument 200, 200''' that is not engaged by the rotatable element 40 may remain stationary or move independently from the rotatable element 40 as the rotatable element 40 rotates.

In other embodiments, the conduit 55 serves as an intermediate channel between the elongated medical instrument and the flow facilitating apparatus. With continued reference to FIG. 17, the conduit 55 may establish communication between a first elongated medical instrument 200''' (e.g., a catheter, etc.) at a distal end of the rooter 10' and a second elongated medical instrument 200'''' at a proximal end of the rooter 10'. Such an arrangement may be used in conjunction with a third elongated medical instrument 200 that extends through the first elongated medical instrument 200'''.

In the embodiment depicted by FIGS. 4A-4C, the rotatable element 40 includes an intermediate portion 45, as well as a distal portion 42 and a proximal portion 50 at opposite ends of the intermediate portion 45.

The intermediate portion 45, which may be generally cylindrical in shape, includes a rotation facilitator 47. In the illustrated embodiment, the rotation facilitator 47 comprises a helical ridge, which protrudes from an outer surface 46 of the intermediate portion 45. In particular, the rotation facilitator 47 may wrap circumferentially around the intermediate portion 45. The rotation facilitator 47 may be continuous, as illustrated, or it may comprise a discontinuous structure. The rotation facilitator 47 extends along at least a portion of the length of the intermediate portion 45. In some embodiments, the rotation facilitator 47 may extend along only a part of the intermediate portion 45, as in the depicted embodiment, where the ends of the rotation facilitator 47 are spaced apart from corresponding ends of the intermediate portion 45.

The pitch of the rotation facilitator 47 may be configured to impart the rooter 10 with a desired number of rotations per stroke (i.e., full movement of the actuator 90 along the length of the rotatable element 40). For example, a rotation facilitator 47 with a relatively large pitch may cause the rotatable element 40 to rotate more slowly, with greater torque, and with fewer revolutions per stroke (e.g., about 1½ revolutions per stroke, about 1 revolution per stroke, etc.) than a rotation facilitator 47 with a smaller pitch. When faster rotation or an increase in revolutions per stroke (e.g., five revolutions per stroke or more, etc.) is desired, the pitch of the rotation facilitator 47 may be decreased.

The rotation facilitator 47 may be configured in a manner that facilitates the use of certain processes in the manufacture of the rotatable element 40. For example, one or more surfaces of the helical ridge may be flattened to facilitate the use of injection molding processes to manufacture the rotatable element 40.

Figures 7A, 7B, 7C:
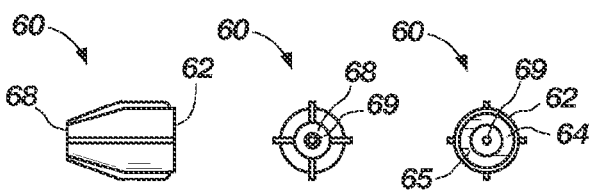
FIGS. 7A, 7B, and 7C are side, distal end, and proximal end views of a distal retention element of the embodiment of rooter illustrated by FIGS. 1 and 2.

The distal portion 42 of the rotatable element 40 may also be cylindrical in shape. In the embodiment shown in FIGS. 4A-4C, the distal portion 42 of the rotatable element 40 has a smaller diameter than the intermediate portion 45 of the rotatable element 40. Thus, a circumferential ledge 44 is present at the boundary between the distal portion 42 and the intermediate portion 45. The distal portion 42 may also be configured to pass through the opening 28 in the distal end 30 of the housing 20 (FIGS. 3A and 3C), and to protrude from the distal end 30. The distal portion 42 of the rotatable element 40 may be configured to engage or be engaged by the distal retention element 60 (FIGS. 7A-7C). In this regard, a distal portion 42 of some embodiments of a rotatable element 40 of a rooter 10 may include one or more retention features 43, such as the helical thread shown in FIG. 4A.

The proximal portion 50 of the rotatable element 40 may likewise have a cylindrical shape. In some embodiments, the proximal portion 50 may be configured to protrude beyond the proximal end 30 of the housing 20 of a rooter 10. The proximal portion 50 may be configured to engage or be engaged by the proximal retention element 70 (FIGS. 6A-6D). Such engagement may, in some embodiments, be at least partially enabled by at least one retention feature 52, such as the helical thread illustrated by FIG. 4A.

A circumferential rim 54, which extends around and protrudes from the outer surface 46 of the rotatable element 40, may delimit, or define a boundary between, the intermediate portion 45 of the rotatable element 40 and its proximal portion 50. The circumferential rim 54 may provide a stop for an actuator 90 (FIGS. 8A-8C) that cooperates with the rotatable element 40 and is configured to cause the rotatable element 40 to rotate about its longitudinal axis 41.

Figures 5A, 5B, 5C, 6A, 6B, 6C, 6D:
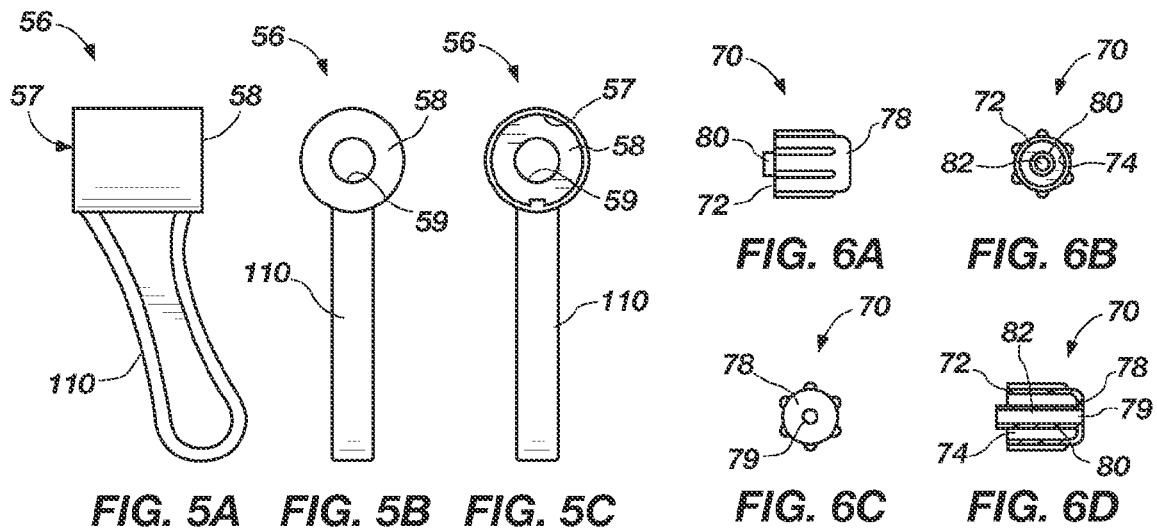
FIGS. 5A, 5B, and 5C are side, rear, and front views, respectively, of a cap of the embodiment of rooter illustrated by FIGS. 1 and 2.
FIGS. 6A, 6B, and 6C are, respectively, side, distal end, and proximal end views of a proximal retention element of the embodiment of rooter shown in FIGS. 1 and 2.
FIG. 6D is a cross-section taken through the length of the proximal retention element depicted by FIGS. 6A-6C.

In some embodiments, a rooter 10 (FIGS. 1 and 2) may include a cap 56 configured to cooperate with the circumferential rim 54 to retain the rotatable element 40 within the interior of the housing 20. An embodiment of cap 56 that may be used as part of the rooter 10 (FIGS. 1 and 2) is shown in FIGS. 5A-5C. The cap 56 may be configured to be disposed over the opening 32 (FIGS. 3A and 3C) in the proximal end 30 of the housing 20. In a specific embodiment, the cap 56 may include a receptacle 57 that receives the proximal end 30 of the housing 20. An interior surface of an end 58 of the cap 56 may be configured to abut the circumferential rim 54 (FIGS. 4A and 4C) of the rotatable element 40 and an edge of the proximal end 30 of the housing 20, while an aperture 59 through the end 58 of the cap 56 may be configured to receive the proximal portion 50 of the rotatable element 40.

FIG. 1B depicts a variation of the rooter 10, in which a proximal surface of the circumferential rim 54 at the proximal end of the rotatable element 40 and the interior surface of the end 58 of the cap 56 include cooperating features 54*f* and 58*f*. Without limiting the scope of this disclosure, the cooperating features 54*f* and 58*f* may comprise convex nubs and the same number of correspondingly positioned concave recesses. The cooperating features 54*f* and 58*f* may be configured to cause the rotatable element 40 to repeatedly move back and forth (distally and proximally) along its longitudinal axis 41 during rotation of the rotatable element 40. Thus, the cooperating features 54*f* and 58*f* may be configured to cause a hammering action in the rotatable element 40, as well as in any elongated medical instrument secured to the rotatable element 40, during rotation. The cooperating features 54*f* and 58*f* may engage each other as the actuator 90 (FIG. 1) is pulled proximally, but not while the actuator 90 is pushed distally. In some embodiments, a spacing element, such as a coiled spring, may be positioned between circumferential rim 54 and the end 58 of the cap 56 to ensure that the cooperating features 54*f* and 58*f* do not engage each other while the actuator 90 is pushed distally. Alternatively, various elements of the rooter 10 may be configured to impart the rotatable element 40 with a hammering action regardless of the direction in which the actuator 90 is moved or the rotatable element 40 rotates (e.g., by minimizing dimensional tolerances, by providing similar elements and features at or near the distal end of the rooter 10, etc.).

In some embodiments, a fixed handle 110 may protrude from the cap 56. A configuration of the fixed handle 110 may enable a user to at least partially grasp the rooter 10 (FIGS. 1 and 2) or hold it in place with a thumb or palm.

The cap 56 may, in some embodiments, be held in place on the proximal end 30 of the housing 20 by way of the proximal retention element 70, an embodiment of which is depicted in FIGS. 6A-6D. The proximal retention element 70 is configured to be coupled with the proximal portion 50 (FIGS. 4A and 4C) of the rotatable element 40. More specifically, the proximal retention element 70 may have the appearance of a cap, with an open distal end 72 and a receptacle 74 that are configured to receive the proximal portion 50 of the rotatable element 40. In addition, at an opposite end of the receptacle 74 from the open distal end 72, the proximal retention element 70 may have a substantially closed proximal end 78.

The receptacle 74 may be configured to engage or to be engaged by the proximal portion 50 (FIGS. 4A and 4C) of the rotatable element 40. In a specific embodiment, the receptacle 74 may include at least one retention feature (not shown), such as a helical thread on an interior surface 75 of the receptacle 74, configured to mutually engage a corresponding retention feature 52 of the proximal portion 50 of the rotatable element 40.

An opening 79 may extend through the proximal end 78 of the proximal retention element 70. In some embodiments, such as that illustrated by FIGS. 6A-6D, the proximal retention element 70 and, in a particular embodiment, its opening 79 may be configured to receive and engage an elongated medical instrument, such as a wire (e.g., a guide wire, a wire used for other purposes, etc.), a catheter, or another elongated element that may be used to enable or effect a medical procedure within the body of a subject. In the illustrated embodiment, the opening 79 through the proximal end 78 of the proximal retention element 70 communicates with a conduit 82 of a male member 80. The male member 80 extends through the receptacle 74 of the proximal retention element 70. When used with an embodiment of rotatable element 40 (FIGS. 4A-4C) that includes a conduit 55, the male member 80 of the proximal retention element 70 may be configured for insertion into the conduit 55.

In some embodiments, the proximal retention element 70 may be configured to engage an elongated medical instrument 200 (FIG. 15) in a manner that causes the elongated medical instrument 200 to rotate as the proximal retention element 70 rotates. For example, and not to limit the scope of this disclosure, the surfaces that define the opening 79 through the proximal end 78 of the proximal retention element 70 may be configured to lock onto, grasp, or engage a surface 208 of the elongated medical instrument 200. As another non-limiting example, the elongated retention element 70 may include one or more features (e.g., a retention slot, a locking feature, etc.) that communicate or are otherwise associated with the opening 79 through the proximal end 78 to enable selective locking, grasping, or other engagement of the surface 208 of the elongated medical instrument 200. In yet another non-limiting example, the proximal retention element 70 may be configured to couple with a separate device (not shown) that locks onto, grasps, or otherwise engages the surface 208 of the elongated medical instrument 200.

The distal retention element 60, an embodiment of which is illustrated by FIGS. 7A-7C, may also have the general appearance of a cap, with an open proximal end 62, an interior receptacle 64 that communicates with proximal end 62, and a substantially closed distal end 68. The proximal end 62 and the receptacle 64 are configured to receive the distal portion 42 (FIGS. 4A and 4B) of the rotatable element 40. In some embodiments, the receptacle 64 includes one or more retention features (not shown), which may be configured to mutually engage a corresponding retention feature 43 of the distal portion of the rotatable element 40, such as a helical thread carried by the surface 65 of the depicted receptacle 64.

The distal end 68 of the distal retention element 60 may include an opening 69, which may be configured to receive an elongated medical instrument 200 (FIG. 15), such as a catheter, wire (e.g., a guide wire, a wire used for other purposes, etc.), a needle, a trocar, or another elongated element that may be used to enable or effect a medical procedure within the body of a subject. When such a distal retention element 60 is configured for assembly with an embodiment of rotatable element 40 (FIGS. 4A-4C) that includes a conduit 55 extending therethrough, the opening 69 through the distal end 68 of the distal retention element 60 may be configured for alignment and/or communication with the conduit 55.

In addition to being configured to receive an elongated medical instrument 200 (FIG. 15), some embodiments of distal retention elements 60 may be configured to lock onto, grasp, or otherwise engage, or at least partially engage, the elongated medical instrument 200. Without limiting the scope of this disclosure, a distal retention element 60 may include a locking element (not shown) at its distal end 68, external or internal (i.e., within the opening 69 in the distal end 68) threading, internal features (e.g., ribs, etc.) that lock onto, grasp, or otherwise engage an outer surface 208 of the elongated medical instrument 200, other locking features, or the distal retention element 60 may be configured to couple with a separate device (not shown) that locks onto, grasps, or otherwise engages the surface 208 of the elongated medical instrument 200.

Figures 8A, 8B, 8C:
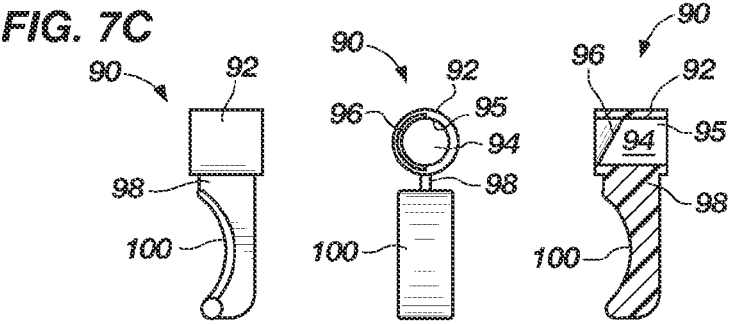
FIGS. 8A and 8B are side and front views, respectively, of an actuator of the embodiment of rooter shown in FIGS. 1 and 2.
FIG. 8C is a cross-section through the length of the actuator shown in FIGS. 8A and 8B.

Turning now to FIGS. 8A-8C, an embodiment of an actuator 90 that may be used with the embodiments of housing 20 and rotatable element 40 shown in FIGS. 4A-4C is illustrated. In particular, the actuator 90 may be configured to interact with the rotatable element 40 in a manner that causes the rotatable element 40, when assembled with the housing 20, to rotate about its longitudinal axis 41. In various embodiments, the actuator 90 includes one or more drive features 96 for causing the rotatable element 40 to rotate.

In the depicted embodiment, the actuator 90 comprises a cylindrical element 92 with an aperture 94 extending through its length. The aperture 94 is configured to receive the rotatable element 40 (FIGS. 4A-4C) and, more specifically, to receive the intermediate portion 45 of the rotatable element 40, enabling the cylindrical element 92 of the actuator 90 to move along the length of the rotatable element 40. The interior surface 95 of the cylindrical element 92—i.e., the surface of the aperture 94—may define one or more drive features 96. In the specific embodiment shown in FIGS. 8B and 8C, the drive features 96 may be configured to engage a corresponding rotation facilitator 47 of the intermediate portion 45 of the rotatable element 40. More specifically, the drive features 96 may engage the rotation facilitator 47 of the intermediate portion 45 of a rotatable element 40.

In addition to including an element configured to cause the rotatable element 40 to rotate, an actuator 90 of a rooter 10 may include an intermediate element 98, which may be configured to reside within and move back and forth through the longitudinal slot 34 in the housing 20.

On an opposite side of the intermediate element 98, the actuator 90 may include a manual trigger 100, which may be engaged by a portion of a user's hand, such as a phalange (e.g., a thumb or finger). In embodiments where the external element comprises a manual trigger 100 configured to be engaged by a user's index finger, the rooter 10 may also include an elongated handle, such as the fixed handle 110 depicted in FIGS. 5A-5C. The elongated handle 110 may be configured to be grasped by at least a portion of the remainder of the user's hand (e.g., the user's palm, remaining fingers and/or thumb, etc.).

In some embodiments, such as that depicted by FIG. 1, a rooter 10 that incorporates teachings may also include a return element 101, such as a spring, that causes the actuator 90 and its manual trigger 100 to return to or substantially return to an initial position. When the manual trigger 100 is moved in a first direction (e.g., proximally, etc.), energy may be stored in the return element 101. When the manual trigger 100 is released, the resilience of the return element 101, and the energy stored within the return element 101, may cause the actuator 90, including the manual trigger 100, to move in an opposite, second direction (e.g., distally, etc.) along the lengths of the housing 20 and the rotatable element 40 of the rooter 10. As illustrated by FIG. 1, the return element 101 may comprise an internal compression spring, which, in the depicted embodiment, is compressed between an edge of the cylindrical element 92 of the actuator 90 and an interior surface of the end 58 of the cap 56 as the manual trigger 100 and, thus, the cylindrical element 92 are drawn proximally along the rotatable element 40 and the housing 20.

In another embodiment, which is depicted by FIG. 1A, a rooter 10 may include a return element 101' with two members 101A' and 101B'. Initially, with the members 101A' and 101B' of the return element at rest (or as close to rest as possible), the actuator 90 may be positioned at an intermediate position along the length of the rotatable element 40 of the rooter 10. One of the members 101A' of the return element 101' may be located on a first (e.g., distal) side of the actuator 90 of the rooter 10, while the other member 101B' of the return element 101' may be located on an opposite, second (e.g., proximal) side of the actuator 90. In a specific embodiment, each member 101A', 101B' may comprise a coiled spring disposed along and around a least a portion of the length of the rotatable element 40. In such an embodiment, proximal movement of the actuator 90 may compress member 101B', which will store energy within member 101B'. When the proximal force is released from the actuator 90, the energy stored within member 101B' may urge the actuator 90 distally toward its original position along the length of the rotatable element 40. Conversely, distal movement of the actuator 90 will compress member 101A'. Once the distal force is removed from the actuator 90, energy stored within member 101A' will force the actuator 90 back toward the proximal end of the rooter 10, substantially to its original position along the length of the rotatable element 40 of the rooter 10.

Return elements that are centered around the rotatable element 40, such as the compression spring embodiments of the return elements 101, 101' shown in FIGS. 1 and 1A, enable the internal cylindrical element 92 of the actuator 90 to remain concentric or substantially concentric with the longitudinal axis 41 of the rotatable element 40. Thus, such a return element prevents cocking of the actuator 90 relative to the rotatable element 40 and facilitates smooth strokes as the actuator 90 moves along the length of the rotatable element 40. Of course, other embodiments of return elements 101, including other types of internal springs, external springs (e.g., a torsion spring, which, in the embodiment depicted by FIG. 1, may be positioned between the manual trigger 100 and the fixed handle 110 or equivalent features, etc.), and other apparatus that will cause the actuator 90 to automatically reverse its position.

In some embodiments, the automatic return of the actuator 90 to its initial position may also cause the rotatable element 40 to rotate in its opposite direction.

In other embodiments, including embodiments where movement of the rotatable element 40 in a single direction (e.g., clockwise or counterclockwise) is desired or oscillatory movement of the rotatable element 40 is not desired, the actuator 90 of a rooter 10 may be configured to return to its initial position without causing further rotation of the rotatable element 40. Without limiting the scope of this disclosure, an actuator 90 may disengage the rotation facilitator 47 of the rotatable element 40 as the actuator 90 returns to its initial position, or the actuator 90 may otherwise be configured to return to its initial position without disengaging the rotation facilitator 47 (e.g., the actuator 90 may include a ratchet mechanism that allows it to return to its initial position without disengaging the rotation facilitator 47, etc.).

Returning reference to FIG. 2, assembly of a rooter 10 that includes the above-described elements may be accomplished by assembling the rotatable element 40 and the actuator 90. The distal portion 42 of the rotatable element 40 may be introduced into and through the aperture 94 of the cylindrical element 92 of the actuator 90. As the rotatable element 40 is pushed distally through the aperture 94, the drive features 96 of the actuator may engage the helical ridge 47 that protrudes from the outer surface 46 of the intermediate portion 45 of the rotatable element 40.

Assembly of the housing 20 and the actuator 90 may include introduction of the cylindrical element 92 of the actuator 90 into the opening 32 at the proximal end 30 of the housing, with the intermediate element 98 of the actuator 90 located within the longitudinal slot 34 through the housing 20. The manual trigger 100 is, of course, located outside of the housing 20, and protrudes from the housing 20.

The distal portion 42 of the rotatable element 40 may be introduced into the opening 32 at the proximal end 30 of the housing 20 to assemble the rotatable element 40 with the housing 20. The distal portion 42 of the rotatable element 40 is then moved distally through the interior 24 of the housing 20, until the distal portion 42 reaches the distal end 26 of the housing 20. The distal portion 42 of the rotatable element 40 may then be introduced into and through the opening 28 in the distal end 26 of the housing 20, until the distal portion 42 of the rotatable element 40 protrudes from the distal end 26 of the housing 20.

With the distal portion 42 of the rotatable element 40 protruding from the distal end 26 of the housing 20, the longitudinal position of the rotatable element 40 within the interior 24 of the housing 20 may be fixed or substantially fixed by coupling the distal retention element 60 to the distal portion 42 of the rotatable element 40.

When the housing 20 and the rotatable element 40 are assembled, the proximal portion 50 of the rotatable element 40 protrudes beyond the proximal end 30 of the housing 20. To hold the rotatable element 40 and the actuator 90 within the interior 24 of the housing 20, the cap 56 may then be placed over the proximal end 30 of the housing 20. More specifically, the receptacle 57 of the cap 56 may be positioned over the proximal end 30 of the housing 20. Additionally, the proximal portion 50 of the rotatable element 40 may be aligned with the opening 59 (FIGS. 5B and 5C) through the end 58 of the cap 56. As the cap 56 moves distally relative to the housing 20 and the rotatable element 40, the proximal portion 50 of the rotatable element 40 may be positioned around proximal portion 50 of the rotatable element 40.

The cap 56 may be held in place relative to the proximal end 30 of the housing 20 by coupling the proximal retention element 70 to the protruding proximal portion 50 of the rotatable element 40.

Other embodiments of rooters that incorporate teachings of this disclosure are shown in FIGS. 9-13. Features of those embodiments may, unless otherwise described, operate in the same manner or in a manner similar to the corresponding elements of the rooter 10 that has been described in reference to FIGS. 1-8C.

Figure 9:
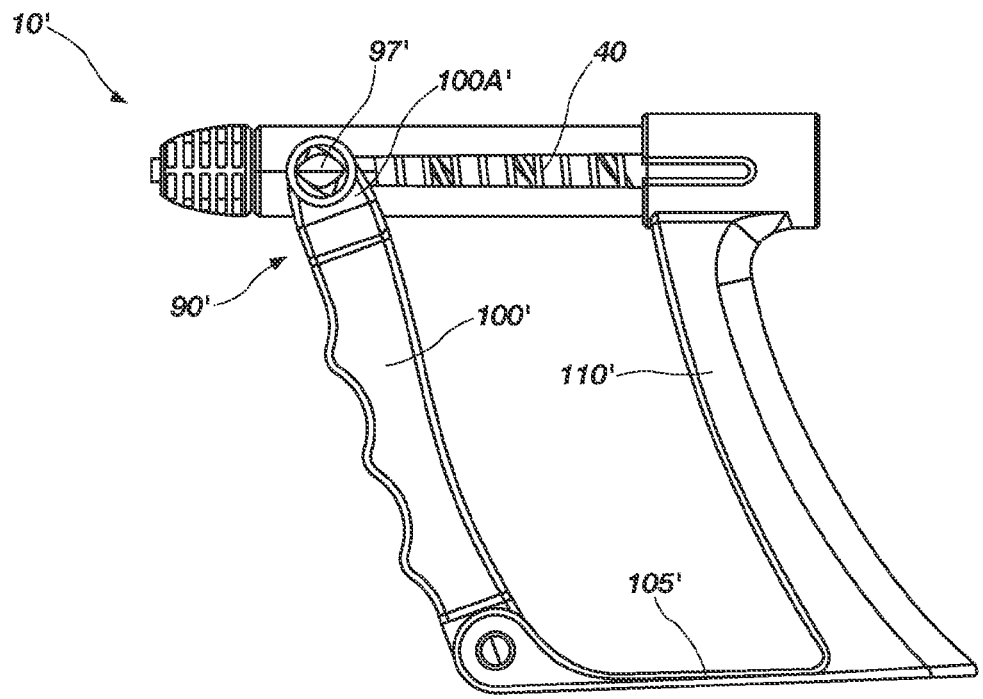
FIG. 9 is a perspective view of an embodiment of rooter in which the actuator includes a spring-loaded actuator or a spring-loaded handle.

In the embodiment depicted by FIG. 9, a rooter 10' that incorporates teachings of the present disclosure may include an actuator 90' with an elongated external element 100' configured for engagement by one or more of a user's fingers, an elongated handle 110' configured to be held by the user's palm or between the user's thumb and index finger, and an intermediate element 105' connecting a lower portion (e.g., bottom end, etc.) of the handle 110' to a lower portion (e.g., bottom end, etc.) of the external element 100'.

The external element 100' of the actuator 90' may be hingedly associated with an internal element 97' of the actuator 90'. More specifically, the external element 100' of the actuator 90 may include a pair of spaced apart members 100A' and 100B' (not shown) that are configured to be located on opposite sides of the internal element 97'. The axis about which the spaced apart members 100A' and 100B' pivot relative to the intermediate element 97' and relative to the actuator 90 may be oriented perpendicular to and intersect the axis of rotation of the rotatable element 40. Such an arrangement may prevent side-to-side, or lateral, movement, or "cocking," of the rooter 10 while the external element 100' is pulled in a proximal direction.

The external element 100' of the actuator 90' may also be hingedly associated with the intermediate element 105', but more fixedly associated with the handle 110', with the intermediate element 105' serving as a cantilevered arm of extending transversely from the handle 110'. In embodiments where the intermediate element 105' may flex relative to the handle 110', the intermediate element 105' may be configured to serve as a spring, absorbing energy when the external element 100' of the actuator is drawn proximally (i.e., toward a user, away from a subject, etc.) and urging the external element 100' in the opposite, distal direction. Alternatively, the intermediate element 105' and the handle 110' may be hingedly associated with one another.

Figure 10:
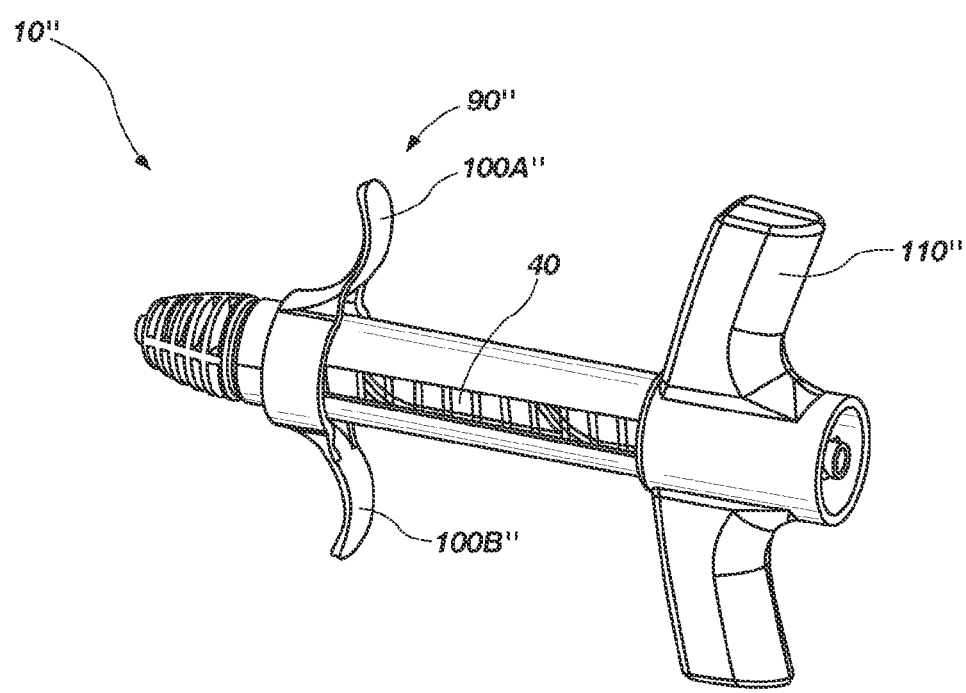
FIG. 10 is a perspective view of rooter with an actuator that includes external elements that extend from opposite sides of the rooter.

Another embodiment of actuator 90", which is shown in FIG. 10, includes a pair of opposed external elements 100A" and 100B". The external elements 100A" and 100B" may be diametrically opposed to one another, or otherwise oriented to enable the actuator 90" to be pulled proximally without substantially moving the location of the axis of the rotatable element 40. The external elements 100A" and 100B" may be configured to be engaged by two of a user's fingers (e.g., the user's index finger and middle finger, etc.). Such an actuator 90" may be accompanied by a handle 110" at or near a proximal end of the rooter 10". The handle 110" may be configured to rest against the palm of a user's hand as the user's fingers grasp the external elements 100A" and 100B" of the actuator 90". Such an embodiment may enable a user to rotate the rooter 10" about its longitudinal axis and/or optimize the force that may be applied distally by the rooter 10".

Figure 11A:
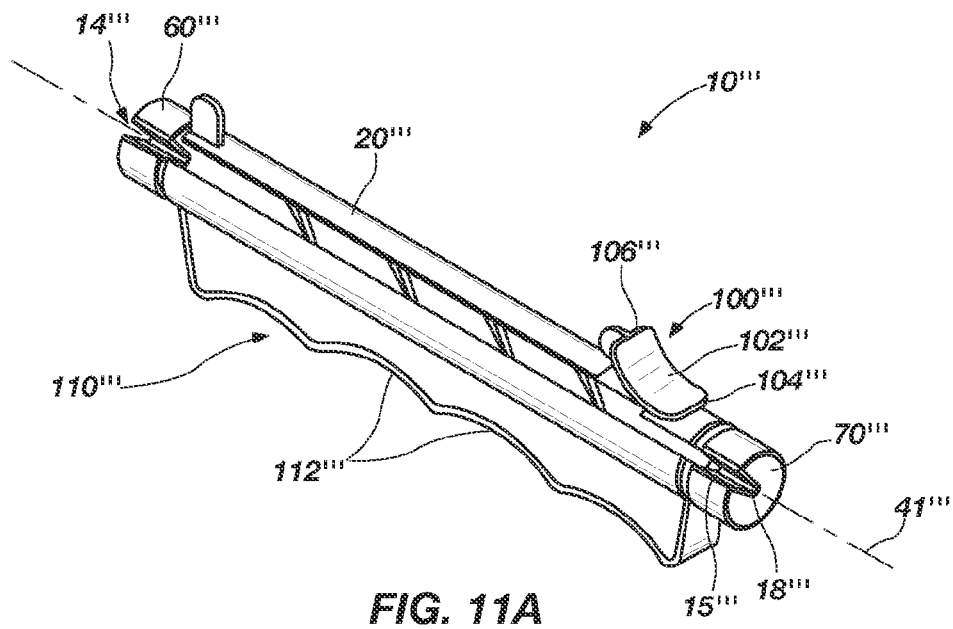
FIGS. 11A-11C are perspective, proximal end, and cross-sectional views, respectively, of another embodiment of rooter.
Figure 11B:
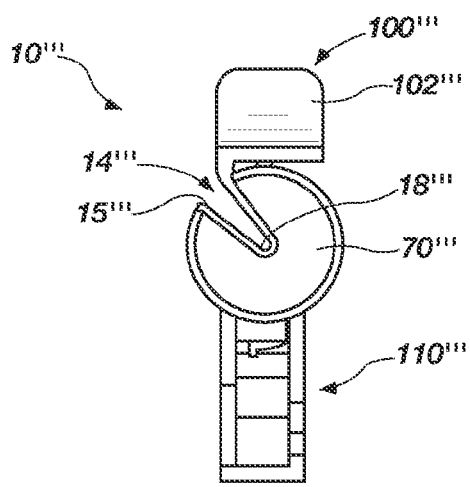
Figure 11C:
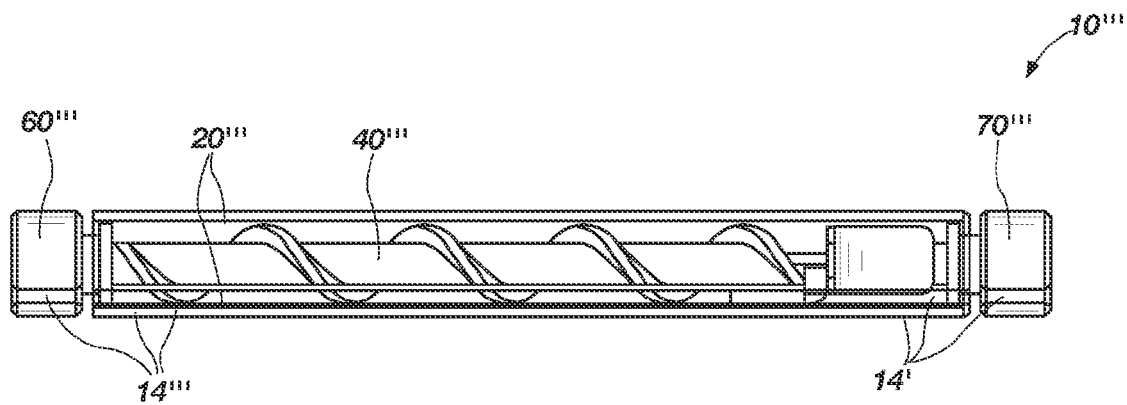

In FIGS. 11A-11C, an embodiment of rooter 10''' is depicted that includes a longitudinal slot 14''' that extends the entire length of the device. The longitudinal slot 14''' includes portions that extend through the distal retention element 60''', the housing 20''' and rotatable element 40''', and the proximal retention element 70'''. In the depicted embodiment, the longitudinal slot 14''' is wider at its opening 15''' (i.e., at the surfaces or circumferences of one or more of the distal retention element 60''', the housing 20''' (and, optionally, the rotatable element 40'''), and the proximal retention element 70''') than at its closed edge 18''', which, in some embodiments, may be located at or extend to a location just beyond a longitudinal axis 41''' of the rotatable element 40''' of the rooter 10'''. Slots 14''' that are tapered in this manner may be configured to receive and retain (e.g., by interference fit, etc.) elongated medical instruments 200 (FIG. 15) of a variety of different diameters or gauges.

FIGS. 11A-11C also illustrate another embodiment of manual trigger 100''' and handle 110''' that may be used with a rooter (e.g., rooter 10''', etc.). The manual trigger 100''' includes a concave surface 102''' with a proximal portion 104''' oriented generally parallel with the housing 20''' of the rooter 10''' and a distal portion 106''' extending away from the housing 20'''. The configuration and orientation of the manual trigger 100''' enable it to be easily moved along the length of the housing 20''', particularly when a user wraps his or her fingers around the housing 20'''. In order to accommodate the user's fingers, and to enhance the user's grasp on the housing 20''', a handle 110''' may be positioned on an opposite or substantially opposite (e.g., diametric, etc.) side of the housing 20''' from the manual trigger 100'''. In the depicted embodiment, the handle 110''' is an elongated element with a plurality of concave indentations 112''' for receiving the user's fingers.

Figure 12:
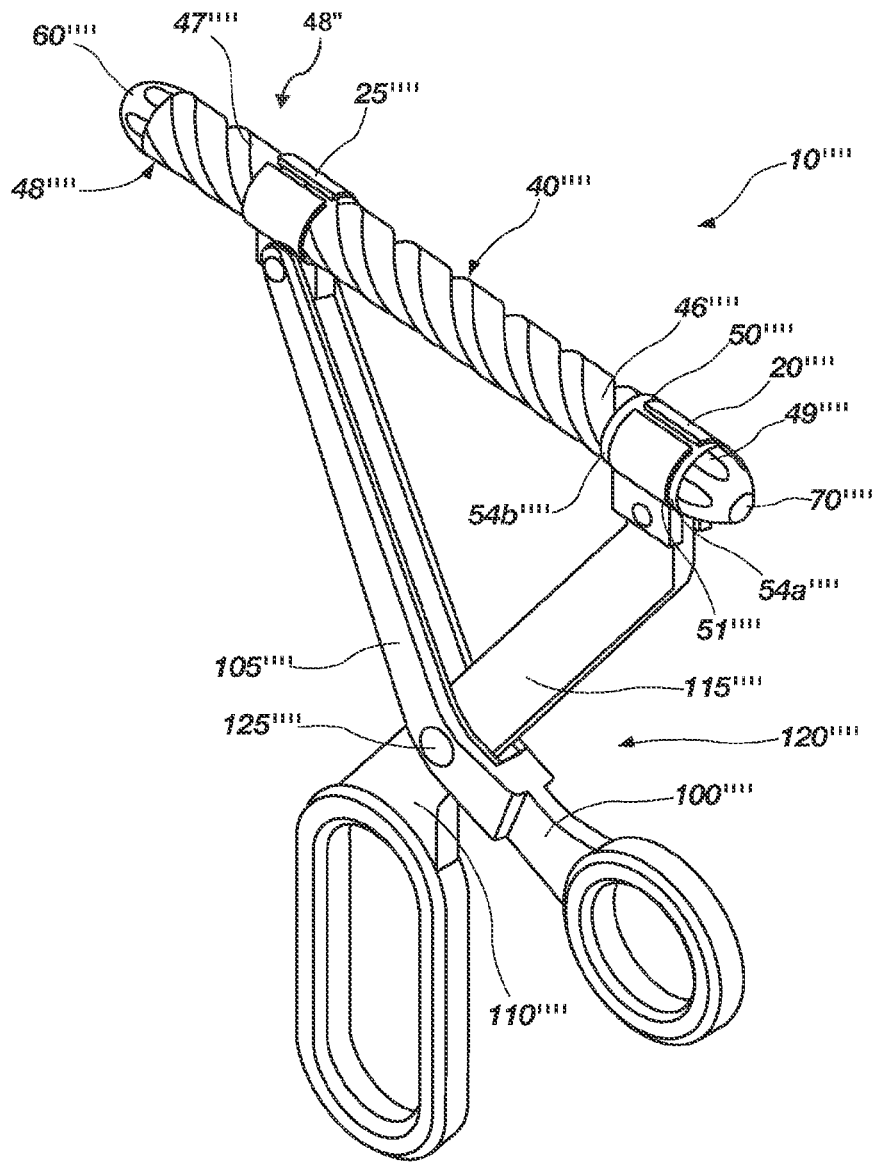
FIG. 12 illustrates an embodiment of rooter with a pair of connected handles.

Referring now to FIG. 12, an embodiment of rooter 10'''' that lacks a housing, and includes a scissors-like handle 120'''' is shown. Instead of a housing, rooter 10'''' includes a stationary sleeve 20'''' and a translatable sleeve 25''''. The stationary sleeve 20'''' and the translatable sleeve 25'' both include cylindrical openings.

The stationary sleeve 20'''' is configured to be longitudinally retained within a retention section 51'''' of a rotatable element 40'''' of the rooter 10''''. The retention section 51'''' is defined by a pair of spaced apart circumferential rims 54a'''' and 54b'''' protruding from the outer surface 46'''' of the rotatable element 40'''', and a smooth, cylindrically shaped portion of the outer surface 46'''' located between the circumferential rims 54a'''' and 54b''''. Although the retention section 51'''' is depicted in FIG. 12 as being located near the proximal end 50'''' of the rotatable element 40'''', rotatable elements with retention portions at other longitudinal locations are also within the scope of this disclosure.

The translatable sleeve 25'''' is configured to interact with a rotation facilitator 47'''' of the rotatable element 40''''. In the depicted embodiment, the translatable sleeve 25'''' may be configured like, or similar to, the cylinder 92 of the actuator 90 described in reference to FIGS. 8A-8C.

Figure 15:
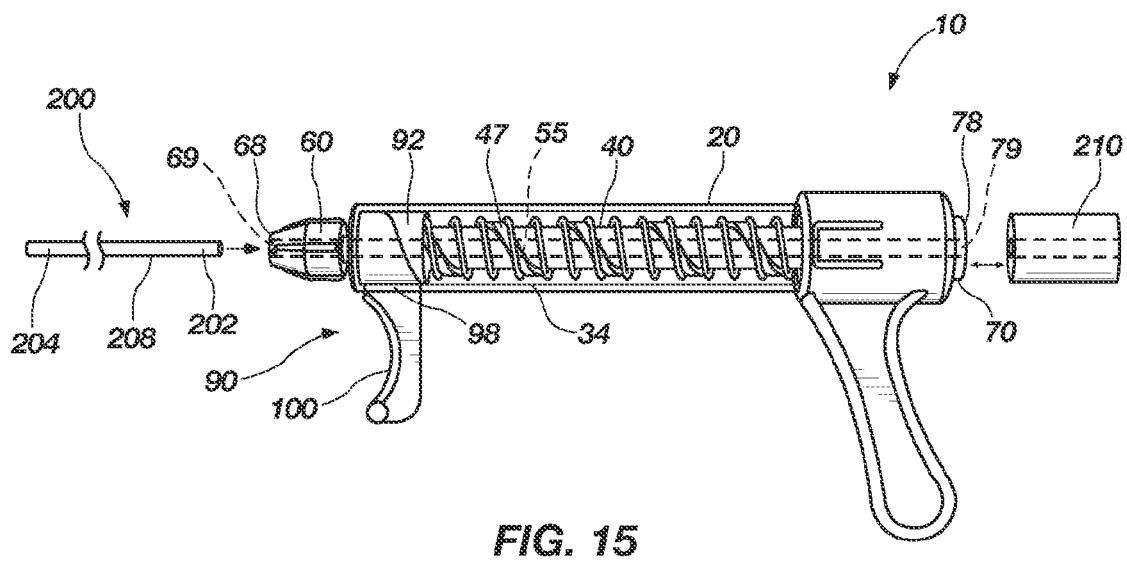
FIG. 15 illustrates an embodiment of a system that includes a rooter and an elongated medical instrument.

Retention elements 60'''' and 70'''' on opposite ends 48'' and 49'', respectively, of the rotatable element 40''. In the depicted embodiment, retention element 60'''' may prevent movement of the translatable sleeve 25'''' beyond its corresponding end 48'''' of the rotatable element 40''''. (Of course, in embodiments where the retention section 51'''' of the rotatable element 40'''' is located at or nearer to a distal portion 42'''' of the rotatable element 40'''', the retention element 70'''' located adjacent to a proximal portion 50'''' of the rotatable element 40'''' may prevent the translatable sleeve 25'''' from moving beyond its corresponding end 49'''' of the rotatable element 40''''). One or both retention elements 60'''' and 70'''' may be configured to engage an elongated medical instrument 200 (FIG. 15).

The handle 120'''' includes two handle members 100'''' and 110''''. The handle members 110'''' and 100'''' extend from the stationary sleeve 20'''' and the translatable sleeve 25'''', respectively. In the depicted embodiment, each handle member 100'''', 110'''' is pivotally associated with its corresponding sleeve 20'''', 25''''. Handle members 100'''' and 110'''' cross at somewhat intermediate locations 105'''' and 115'''', respectively, and are joined to one another at those locations by a hinge 125''''. As the handle members 100'''' and 110'''' are drawn together or forced apart, the translatable sleeve 25'''' interacts with the rotation facilitator 47'' of the rotatable element 40'''', causing the rotatable element 40'''' to rotate.

Figure 13:
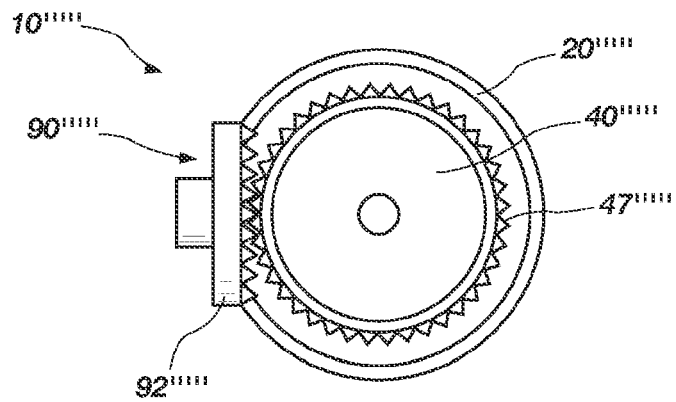
FIG. 13 depicts an embodiment of gear-driven rooter.

In another embodiment, shown in FIG. 13, a rooter 10''''' may include an actuator 90''''' that comprises a rotatable gear 92'''''. As the gear 92''''' of the actuator 90''''' rotates (e.g., by use of a thumb to rotate the actuator 90''''' or a feature thereof, etc.), it engages another gear 47''''' associated with (e.g., surrounding, at least partially surrounding, etc.) the rotatable element 40''''' of rooter 10''''' ((e.g., extending circumferentially around a portion of the rotatable element 40''''', etc.). In such an embodiment, the actuator 90''''' may remain in a stationary position along the length of the rooter 10''''' (i.e., along the lengths of the housing 20''''' and the rotatable element 40''''') as the rotatable element 40''''' rotates.

Figure 14A:
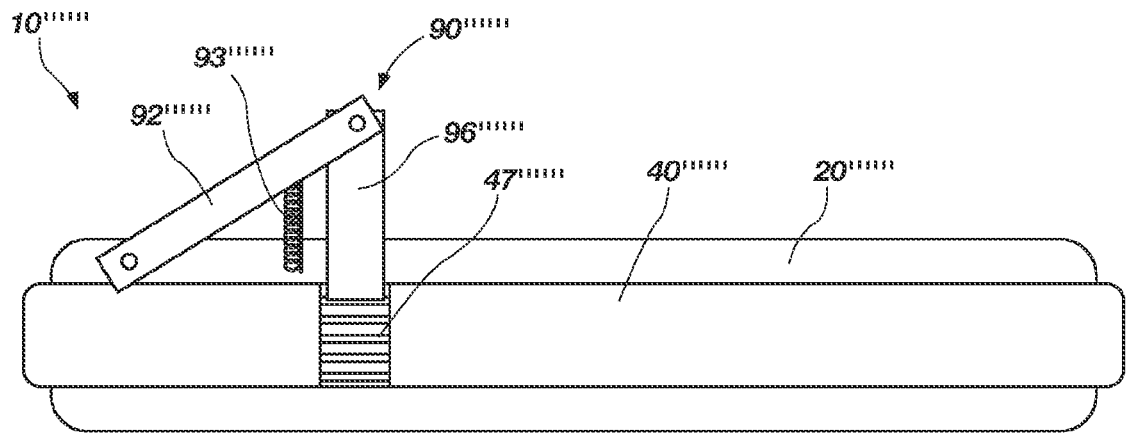
FIGS. 14A-14C shown an embodiment of rooter that rotates under control of a rack and pinion mechanism.
Figure 14B:
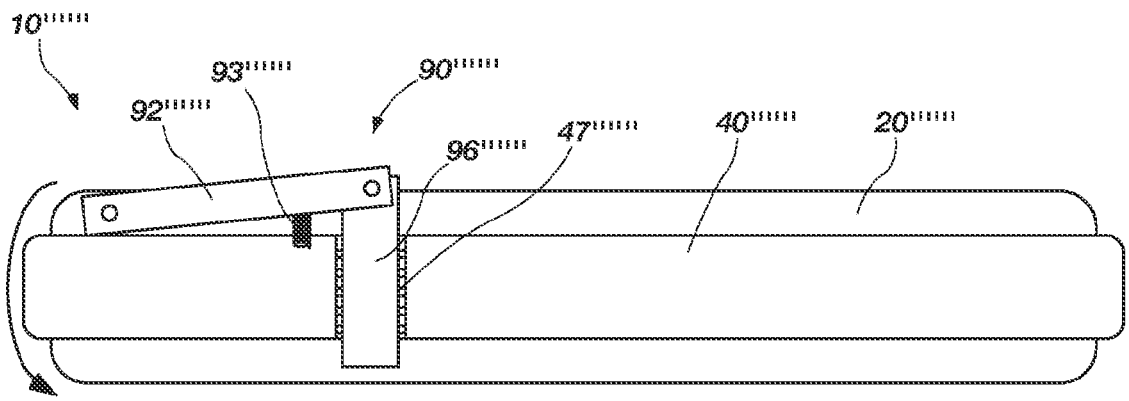
Figure 14C:
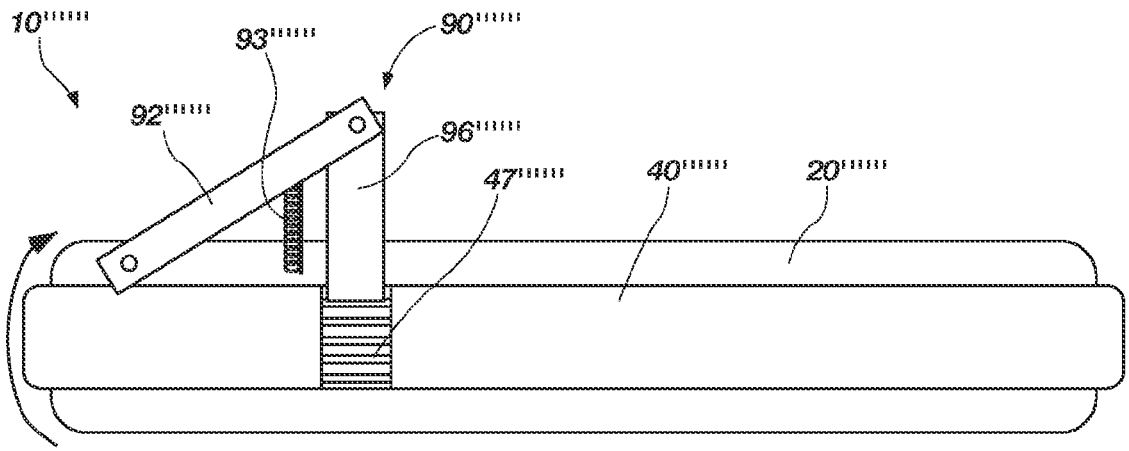

FIGS. 14A-14C depict an embodiment of rooter 10'''''' in which the actuator 90'''''' includes a manual trigger 92'''''' and a gear rack 96''''''. The manual trigger 92'''''' is translatably associated with the housing 20'''''' of the rooter 10'''''' (e.g., pivotally, such as in the depicted embodiment; like a push button, etc.). In various embodiments, the manual trigger 92'''''' may be operated with a user's thumb or finger. In some embodiments, a resilient element 93'''''' (e.g., a spring, etc.) may be associated with the manual trigger 92'''''' in such a way as to cause the manual trigger 92'''''' to return to its initial position after the manual trigger 92'''''' has been depressed or otherwise actuated.

The gear rack 96'''''' of the actuator 90'''''' may be associated with the manual trigger 92'''''' in such a way that, when the manual trigger 92'''''' is depressed or otherwise actuated, the gear rack 96'''''' moves in a desired direction. In the depicted embodiment, depression of the manual trigger 92"""" causes the gear rack 96"""" to move in a first direction across, or transverse to, the length of a rotatable element 40"""" of the rooter 10"""", which is disposed within an interior of the housing 20"""". When the manual trigger 92"""" is released, the resilient element 93"""", if any, may cause the gear rack 96"""" to move in an opposite, second direction across the rotatable element 40"""".

A gear 47"""" with teeth that are configured and spaced to mesh with teeth of the gear rack 96"""" is positioned along the length of the rotatable element 40"""" at a location where the gear 47"""" will cooperate with the gear rack 96"""". As the manual trigger 92"""" moves and causes the gear rack 96"""" to move, the gear rack 96"""" rotates the gear 47"""". Rotation of the gear 47"""", in turn, rotates the rotatable element 40"""", along with any elongated medical instrument 200 (FIG. 15) that has been directly or indirectly coupled to the rotatable element 40.varies."".

Figure 16:
FIG. 16 illustrates an embodiment of mascerator that may be used with a rooter.

A specific embodiment of an elongated medical instrument that may be used with a rooter 10 or another rotation facilitator to break up, or macerate, substances within a subject's body or within another medical device is shown in FIG. 16. The mascerator 200" illustrated by FIG. 16 includes an expanded element 210". The macerator 200" may be manufactured by forming one or more cuts along a portion of the length of a wire, then forcing uncut portions of the wire on opposite sides of the cut(s) toward each other to define the expanded element 210", which may have a basket-like configuration, from the cut portion of the wire. In the depicted embodiment, intersecting cuts are formed along a portion of the length of the wire. More specifically, the cuts may be oriented substantially parallel to one another. Of course, a single cut or more than two cuts may be formed to enable the formation of an expanded element that includes twice as many elements as the number of cuts formed in that section of the wire (e.g., a single cut in the wire may be used to form an expanded element with two elements; two cuts in the wire may be used to form an expanded element with four elements; three cuts in the wire may be used to form an expanded element with six elements; etc.). Some types of wires (e.g., wires formed from nitinol, etc.) may be heat treated to fix or substantially fix the expanded element in a desired configuration.

Figure 18:
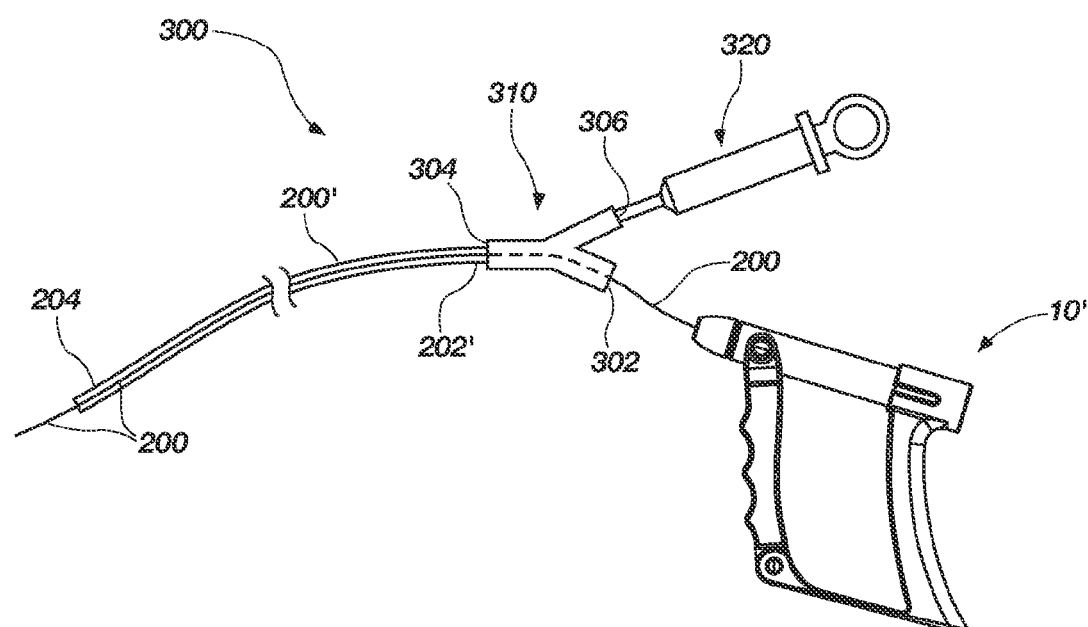
FIG. 18 depicts an embodiment of an assembly that includes a rooter, a plurality of elongated medical instruments, a branched coupling element, and a medical device associated with the branched coupling element in a manner that will cause fluid to flow through at least one of the plurality of elongated medical instruments and, optionally, through a channel extending through the rotatable element of the rooter.

Turning now to FIG. 18, an embodiment of a system 300 for rotating one or more elongated medical instruments 200 is illustrated. The system 300 may include a rooter 10' (or any other suitable embodiment of rooter), a branched coupling element 310 (e.g., a Y-connector, a T-connector, etc.), one or more elongated medical instruments 200, and another medical device 320. In a specific embodiment, a first elongated medical instrument 200, such as a wire, a macerator or a small catheter, may be rotationally coupled to the rotational element 40 (see, e.g., FIG. 9) of the rooter 10'. A proximal end 302 of the branched coupling element 310 may be positioned adjacent to the distal end of the rotational element 40, but remain rotationally uncoupled from the rotational element 40. A proximal end 202' of a second elongated medical instrument 200', such as a catheter or another conduit, which resides coaxially over the first elongated medical instrument 200, may be coupled to a distal end 304 of the branched coupling element 310. Another medical device 320, such as a syringe, an aspirator, or the like, may be coupled to a branch 306 of the branched coupling element 310 and, thus, communicate with the second elongated medical instrument 200''' through the branched coupling element 310. In such an arrangement, the rooter 10' may be used to cause the first elongated medical instrument 200 to rotate, while the other medical device 320 introduces material into and/or withdraws material from the second elongated medical instrument 200'''.

Other arrangements of systems, including arrangements in which two or more elongated medical instruments 200', 200''', etc. are associated with the rooter 10' (see, e.g., FIG. 3) and the branched coupling element 310 positioned proximal to the rooter 10' (e.g., in communication with the elongated medical instrument 200'''' shown in FIG. 17) are also within the scope of this disclosure.

With returned reference to FIG. 17, some embodiments of use of a rooter according to this disclosure (rooter 10' is shown, merely to provide an example) to rotate elongated medical instruments 200 and to perform various procedures, including medical procedures, are disclosed. Non-limiting examples of elongated medical instruments 200 that may be used with the rooter 10 include wires (e.g., guide wires, etc.), mascerators, needles, drill bits, trocars, catheters and other elongated medical instruments that may be used to enable or effect medical procedures within the body of a subject. Depending upon their intended or desired use, these elongated medical instruments may be configured with a variety of tips or distal elements, or with accessories such as balloons, brushes, stents, electrodes, sensors, cutting elements, optics, or wiring.

Since the rooter 10 is configured to be used with a plurality of different elongated medical instruments, it provides a healthcare provider with a great deal of flexibility in selecting a specific elongated medical instrument with which he or she prefers to perform a certain procedure. As an example, a doctor may have two or three guide wires he or she likes to use in a catheterization procedure. The rooter 10 is configured to enable the doctor to choose his or her preferred wires.

In use, a proximal end 202 of an elongated medical instrument 200 may be introduced into an opening 69 in the distal end 68 of the distal retention element 60 of the rooter 10. When the elongated medical instrument 200 comprises a relatively short device, such as a needle, trocar, or the like, insertion of the proximal end 202 of the elongated medical instrument 200 into the opening 69 may at least partially couple the elongated medical instrument 200 to the rooter 10 without inserting the elongated medical instrument 200 further into the rooter 10. In embodiments where the elongated medical instrument 200 comprises a longer device, such as a catheter, wire or the like, its proximal end 202 may be inserted only into the opening 69 of the distal end 68 of the distal retention element 60, or the proximal end 202 may be inserted further into the rooter 10. Without limiting the scope of the present disclosure, the proximal end 202 of the elongated medical instrument 200 may also be pushed proximally through the conduit 55 of the rotatable element 40 of the rooter 10, and through the opening 79 through the proximal end 78 of the proximal retention element 70 of the rooter 10.

With the elongated medical instrument 200 in place, it may be rotationally coupled to the rooter 10. In embodiments where the distal retention element 60 and/or the proximal retention element 70 of the rooter 10 include features that lock onto, grasp, or otherwise engage a surface 208 of the elongated medical instrument 200, rotational coupling of the elongated medical instrument 200 to the rooter 10 occurs during assembly of the elongated medical instrument 200 with the rooter 10. In other embodiments, at least one separate locking device 210 may be assembled with and lock onto, grasp, or otherwise engage the surface 208 of the elongated medical instrument 200, then each locking device 210 may be coupled to the distal retention element 60 or the proximal retention element 70 of the rooter 10. Rotational coupling of the elongated medical instrument 200 to the distal retention element 60 or the proximal retention element 70 may be effected in a manner that causes the elongated medical instrument 200 to rotate as the distal retention element 60 and/or the proximal retention element 70 rotate.

A distal end 204 of the elongated medical instrument 200 may be introduced into a body of a subject at a desired location. In some embodiments, the distal end 204 may be inserted into the subject's body before the elongated medical instrument 200 is assembled with the rooter 10. In other embodiments, the rooter 10 may be assembled with an elongated medical instrument 200 that has already been introduced, or at least partially introduced, into the subject's body.

Rotation of the elongated medical instrument 200 (e.g., about its longitudinal axis etc.) may be effected by causing the rotatable element 40, as well as the distal retention element 60 and/or the proximal retention element 70, to rotate (e.g., about longitudinal axis 41, etc.). In the illustrated embodiment, such rotation may be caused by moving the manual trigger 100 of the rooter 10's actuator 90 along the length of the rooter 10's housing 20. As the manual trigger 100 is moved along the length of the housing 20, the intermediate element 98 of the actuator 90 moves through the longitudinal slot 34 in the housing 20, which causes the cylindrical element 92 of the actuator 90 within the interior 24 of the housing to move along the length of the rotatable element 40. As the cylindrical element 92 moves along the length of the rotatable element 40, drive features 96 (FIGS. 8B and 8C) on or in the interior surface 95 of the aperture 94 of the cylindrical element 92 may engage the complementarily configured rotation facilitator 47 of the rotatable element 40 (e.g., the depicted helical ridge, etc.). The configurations of the longitudinal slot 34 and the actuator 90 (specifically, its intermediate element 98) may prevent rotation of the cylindrical element 92 of the actuator 90 within the interior 24 of the housing 20, or at least enable the rotatable element 40 to rotate relative to the housing 20. During rotation of the rotatable element 40, one or both of the distal retention element 60 and the proximal retention element 70 to rotate relative to the housing 20, which rotation may also cause the elongated medical instrument 200 to spin relative to the housing 20 of the rooter 10. If the rooter 10 is held stationary, or at least substantially stationary, movement of the manual trigger 100 of the actuator 90 of the rooter 10 may cause the elongated medical instrument 200 to rotate or spin relative to a subject's body. In other embodiments, the rooter 10 may be used to rotationally oscillate the elongated medical instrument 200, which may enhance the performance of the device. As an example, oscillation of an elongated medical instrument 200 may cause some vibration or quivering of the elongated medical instrument 200, which may reduce friction during use of the elongated medical instrument 200.

Rotation or oscillation of the elongated medical instrument 200 may be effected during or separately from longitudinal movement (e.g., distal movement, proximal movement, back-and-forth movement, etc.), or hammering movement, of the elongated medical instrument 200. Conversely, hammering movement of an elongated medical instrument 200 may be effected with our without rotation or oscillation of the elongated medical instrument.

When the proximal end 202 of a tubular elongated medical instrument 200 (e.g., a catheter, a tube, etc.) is accessible from or proximally beyond the proximal end of the rooter (e.g., beyond the proximal end 78 of the proximal retention element 70 of the rooter 10, etc.), other activities (e.g., aspiration, infusion, introduction of other elongated medical instruments, etc.) may be effected through the elongated medical instrument 200 while it is assembled with the rooter 10 and, in some embodiments, as the elongated medical instrument 200 is rotated, spun, or oscillated.

In various embodiments, a rooter 10 may be used to enable or effect a variety of medical procedures. Without limiting the scope of the disclosed subject matter, medical procedures in which a rooter may be useful include imaging, drug delivery, feeding, stimulation, recording, pacing, temperature sensing, tissue resection, and implant delivery.

In some embodiments, use of a rooter 10 to manipulate an elongated medical instrument 200 may facilitate initial introduction of the elongated medical instrument 200 into the body of a subject. In other embodiments, an elongated medical instrument 200 may be rotated, spun or oscillated with a rooter 10 to facilitate further introduction of the elongated medical instrument 200 into the body of a subject, or its removal from the subject's body.

In some embodiments, when medical personnel introduce an elongated medical instrument 200 into the body of a subject through the skin, a natural orifice, a surgical access site, or other natural or man-made structure, they may encounter friction or obstructions. Some of the causes of friction or obstructions include, without limitation, tortuous pathways, lesions, viscous fluid (e.g., blood clots, etc.), other devices, and combinations of any of the foregoing. Use of a rooter 10 to twist, spin, or oscillate the elongated medical instrument 200 may counteract any friction that may be encountered as the elongated medical instrument 200 is introduced into the body, or during tracking to facilitate device introduction. As a non-limiting example, a rooter 10 may be used to torque a guide wire, which may enable the guide wire to drill through, or cross, lesions or occlusions within a subject's vasculature. In another example, a rooter 10 may rotate a catheter as the catheter is advanced over a wire into a subject's body, including situations where merely pushing the catheter will not cause it to advance along the wire.

Likewise, when an elongated medical instrument 200 such as a wire or catheter is oscillated during its introduction into or its removal from the body of a subject, the vibration induced in the elongated medical instrument may reduce friction between the elongated medical instrument 200 and the interior surfaces of a hollow organ (e.g., a blood vessel, etc), guide catheter or other element within the subject's body. Such a reduction in the friction may reduce or minimize the effort required by a user to advance or withdraw the elongated medical instrument 200. As a non-limiting example, friction will be present at each location where a wire disposed within a guide catheter contacts the inner surface of the guide catheter (e.g., at the entry site, at each curve of the guide catheter, etc.). Oscillation of the wire as it is advanced or withdrawn may cause the wire to intermittently move away from, or bounce off of, the inner surface of the guide catheter, intermittently eliminating friction at that location.

In still other embodiments, rotation, spinning, oscillation and/or hammering action of an elongated medical instrument 200 with a rooter 10 may break up, or macerate, substances (e.g., clots, blockages, etc.) within the body of a subject or within another medical device (e.g., a tube, catheter, etc.) in the subject's body. By breaking up substances, the rooter 10 and elongated medical instrument 200 facilitate removal of the substances from the subject's body or the medical device within the subject's body.

Oscillation of an elongated medical instrument 200 and the resulting vibration or quivering of the elongated medical instrument 200 may also enable use of the elongated medical instrument 200, or at least improve its ability, to be used to locate any natural or unnatural pathways through an obstruction. When oscillated, the elongated medical instrument 200 may be quickly introduced into and removed from various channels of an obstruction, removing material from the obstruction to increase the dimensions of each channel and, thus, to create or enlarge pathways through the obstruction and/or to facilitate reduction or even removal of the obstruction. Some specific, but non-liming embodiments of procedures in which a rooter may be used include, but are not limited to, "first-use" techniques, in which a guide wire or other flexible elongated medical instrument is oscillated. Oscillatory movement of a guide wire may enable the guide wire to penetrate a blockage (e.g., a plaque, a calcified or resistant lesion, etc.) in a controlled manner. Oscillation of a guide wire may also enable a distal tip of the guide wire to quickly probe a plurality of locations, which facilitates "finding" or identifying paths of least resistance through blockages and tortuous paths. Oscillation may also reduce the tendency of a guide wire or other elongated medical instrument from binding the internal surfaces of a path, such as a vessel, a path through a blockage, a catheter or a tube. Oscillation of a guide wire during its movement through a vessel, catheter or tube may also reduce the risk of perforating a vessel, catheter or tube.

When a healthcare provider uses a rooter in such a way, he or she may sense (e.g., feel, etc.) feedback from the guide wire and, thus, from the conditions that the guide wire has encountered, enabling the healthcare provider to react quickly (e.g., terminate rotation, speed up oscillation, slow down oscillation, etc.) in a manner that will minimize the potential for damage or harm to the patient and that will maximize the effectiveness of the procedure.

Still another example of use of a rooter 10 includes rotation, spinning, oscillation and/or hammering action of a needle, such as a rigid or semi-rigid biopsy needle to facilitate the cutting and removal of tissue or another material from the body of a subject, to access (including intraosseous access, etc.) and/or sample bone marrow, a needle for use in spinal interventions, or a needle for providing general access to an internal location of a subject's body.

Spinning or oscillating a needle can help the needle penetrate, drill and mill through a firm or hard substrate. When used with a needle that includes serrations around the circumference of its distal tip, spinning of the needle by a rooter 10 may enable manual coring of the needle into bone or other hard or firm tissues. Alternatively, or in addition, penetration may be achieved when the rooter 10 causes the needle to move back and forth along its longitudinal axis to generate a hammering action.

A rooter 10 may also be useful for removing leads, such as those used with pacemakers or defibrillators. As leads are removed, rotation, spinning, or oscillation of the leads, or of a sheath that has been introduced over the leads, may cut endothelium or fibrin sheaths that may hinder removal of the leads from the subject's vasculature.

Although the foregoing description contains many specifics, these should not be construed as limiting the scope of any of the appended claims, but merely as providing information pertinent to some specific embodiments that may fall within the scopes of the disclosed subject matter the appended claims. Other embodiments may also be devised which lie within the scopes of the appended claims. Features from different embodiments may be employed in combination. The scope of each claim is, therefore, indicated and limited only by its plain language and the legal equivalents to the claim elements. All additions, deletions and modifications to the disclosed subject matter that fall within the meaning and scopes of the claims are to be embraced thereby.

What is claimed is:

1. A hand powered rooter for introducing an elongated medical instrument into a body of a subject, comprising:
   a housing,
   a rotatable element disposed within the housing and rotatable about a longitudinal axis,
   wherein the elongated medical instrument is couplable to the rotatable element; and
   an actuator including an internal element hingedly coupled to a pair of spaced apart members located on opposite sides of the internal element;
   wherein the pair of spaced apart members extend from a manual trigger, an elongated handle, and an intermediate element fixedly attached to a lower portion of the handle and extending transversely from the handle such that the intermediate element is cantilevered from the handle in a distal direction;
   wherein the trigger is attached to the pair of spaced apart members at a first end of the trigger and the trigger is pivotably attached to the intermediate element at a second end of the trigger; and
   an elongated slot extending through the housing, wherein the elongated slot receives at least a portion of the actuator.

2. The hand powered rooter of claim 1, wherein longitudinal movement of the actuator in a first direction along the longitudinal axis causes rotational movement of the rotatable element.

3. The hand powered rooter of claim 2, wherein the rooter includes a return element configured to return the actuator in a second direction along the longitudinal axis to an initial position, the second direction being opposite the first direction.

4. The hand powered rooter of claim 3, wherein the return element is disposed about the rotatable element proximal of the actuator.

5. The hand powered rooter of claim 3, wherein the first direction is a proximal direction and the second direction is a distal direction.

6. The hand powered rooter of claim 5, wherein movement of the actuator in the proximal direction causes the rotatable element to spin or oscillate.

7. The hand powered rooter of claim 5, wherein movement of the actuator in the distal direction does not cause the rotatable element to spin or oscillate.

8. The hand powered rooter of claim 1, wherein the rotatable element includes an outwardly protruding helical ridge.

9. The hand powered rooter of claim 8, wherein the internal element of the actuator surrounds the rotatable element.

10. The hand powered rooter of claim 1, wherein an axis about which the pair of spaced apart members pivot relative to the internal element is oriented perpendicular to and intersects the longitudinal axis of the rotatable element.

11. A hand powered rooter for introducing an elongated medical instrument into a body of a subject, comprising:
    a housing;

a rotatable element disposed within the housing and rotatable about a longitudinal axis, wherein the elongated medical instrument is couplable to the rotatable element;

an actuator including an internal element surrounding the rotatable element, wherein longitudinal movement of the internal element along the longitudinal axis causes the rotatable element to spin; and a manual trigger including a pair of spaced apart members extending from a first end of the manual trigger, the pair of spaced apart members being located on opposite sides of the internal element and hingedly secured to the internal element, wherein the manual trigger is hingedly secured to a handle of the rooter at a second end of the manual trigger;

wherein translating the first end of the manual trigger proximally along the longitudinal axis moves the internal element longitudinally relative to the handle of the rooter; and wherein an elongated slot extends through the housing, wherein the elongated slot receives at least a portion of the actuator.

12. The hand powered rooter of claim 11, further comprising an intermediate element fixedly attached to a lower portion of the handle and extending transversely from the handle such that the intermediate element is cantilevered from the handle in a distal direction.

13. The hand powered rooter of claim 12, wherein the manual trigger is pivotably attached to the intermediate element at the second end of the manual trigger.

14. The hand powered rooter of claim 11, further comprising a return element configured to return the internal element along the longitudinal axis to an initial position upon release of the manual trigger by an operator.

15. The hand powered rooter of claim 14, wherein the return element is disposed about the rotatable element proximal of the internal element.

16. The hand powered rooter of claim 14, wherein the return element is disposed within the housing and coupled to the handle of the rooter.

17. The hand powered rooter of claim 11, wherein the rotatable element includes an outwardly protruding helical ridge configured to engage the internal element.

18. A hand powered rooter for introducing an elongated medical instrument into a body of a subject, comprising:
a handle;
a housing coupled to the handle;
a rotatable element disposed within the housing, the rotatable element being rotatable about a longitudinal axis, wherein the elongated medical instrument is couplable to the rotatable element;
an actuator surrounding the rotatable element; and
a trigger, wherein a first end of the trigger is pivotably attached to the actuator and a second end of the trigger is pivotably attached to an intermediate member extending distally from the handle of the rooter such that the intermediate member is cantilevered from the handle in a distal direction;
wherein longitudinal movement of the actuator along the longitudinal axis causes the rotatable element to spin or oscillate;
wherein proximal movement of the first end of the trigger moves the actuator in a first direction along the longitudinal axis;
wherein a return element surrounds the rotatable element on a proximal side of the actuator, the return element being configured to return the actuator distally to an initial position upon release of the trigger by an operator; and
wherein the housing includes an elongated slot extending through the housing, wherein the elongated slot receives at least a portion of the actuator.

19. The method of claim 18, wherein the rotatable element includes an outwardly protruding helical ridge engaging the actuator.

* * * * *